United States Patent [19]
Kishi et al.

[11] Patent Number: 5,292,754
[45] Date of Patent: Mar. 8, 1994

[54] TREATMENT FOR HYPERTENSION OR GLAUCOMA IN EYES

[75] Inventors: Morio Kishi, Kyoto; Kimio Takahashi, Nishinomiya; Kenji Kawada, Toyonaka; Yasumasa Goh, Sanda, all of Japan

[73] Assignee: Shionogi & Co., Ltd., Japan

[21] Appl. No.: 948,179

[22] Filed: Sep. 21, 1992

Related U.S. Application Data

[63] Continuation-in-part of Ser. No. 778,983, Nov. 6, 1991, abandoned.

[30] Foreign Application Priority Data

Mar. 8, 1990 [JP] Japan ................... 2-57476

[51] Int. Cl.$^5$ ........................... A61K 31/557
[52] U.S. Cl. .................... 514/530; 514/573; 514/913; 206/828; 560/121; 562/503
[58] Field of Search ................ 514/530, 573

[56] References Cited

U.S. PATENT DOCUMENTS 4,599,353  7/1986  Bito ................... 514/530

FOREIGN PATENT DOCUMENTS 97023    12/1983  European Pat. Off.
2193613   2/1974  France
50-37753  8/1975  Japan
1444971   8/1976  United Kingdom

OTHER PUBLICATIONS

Hamon et al., Tetrahedron Letters, No. 50, pp. 4481–4482 (1975).
Gorman et al., Chemical Abstracts 87(25): 194421c (1977).
Gorman et al., Proc. Natl. Acad. Sci., vol. 74, No. 9, pp. 4007–4011, Sep. 1977, "Inhibition of Human Platelet Thromboxane Synthetase by 9,11-azoprosta-5,-13-dienoic Acid".
Greene et al., Protective Groups in Organic Synthesis, John Wiley & Sons, Inc., "Protection for the Hydroxyl Group, Including 1,2-and 1,3-diols" (1991).
Corey et al., Journal of the American Chemical Society, 93:6, Mar. 24, 1971, "Stereospecific Total Synthesis of Prostaglandins E$_3$ and E$_3\alpha$".
Goh et al., Japanese Journal of Ophthalmology, vol. 32, pp. 471–480, 1988, "Effects of Prostaglandin D$_2$ and its Analogues on Intraocular Pressure in Rabbits".
Granström et al., Prostaglandins and Related Substances, pp. 7–13, IRL Press Limited, "Metabolism of Prostaglandins and Lipoxygenase Products: Relevance for Eicosanoid Assay" (1987).
Ohuchida et al., TET, vol. 39, No. 24-P, p. 4263, "Synthesis of Thromboxane A$_2$ Analogs-2" (1982).
Prostaglandins: An Introduction to Their Biochemistry, Physiology and Pharmacology, pp. 23–27, 1976, Elsevier/North-Holland Biomedical Press, "Catabolism of Prostaglandins".
Ohuchida et al., J. Am. Chem. Soc., 1981, 103, pp. 4597–4599, "Synthesis of Trhomboxane A$_2$ Analogues: DL-9,11:11,12-Dideoxa-9,11:11,12-diepithiothromboxane A$_2$".
Collins, Journal of Medicinal Chemistry, vol. 29, No. 4, Apr. 1986, "Development and Therapeutic Role of Synthetic Prostaglandins in Peptic Ulcer Disease".

Primary Examiner—Robert Gerstl
Attorney, Agent, or Firm—Wegner, Cantor, Mueller & Player

[57] ABSTRACT

The present invention relates to a method for treating hypertension or glaucoma in the eye comprising contacting the surface of the eye with a therapeutic amount of a 15-deoxyprostaglandin derivative of the formula (I):

$$\text{A} \diagup\!\!\!\diagdown \text{CH}_2\text{CH}=\text{CH}(\text{CH}_2)_3\text{COOR}^1 \quad \text{R}^2 \quad (I)$$

in which (Abstract continued on next page.)

is a 5 membered ring which is selected from a group consisting of

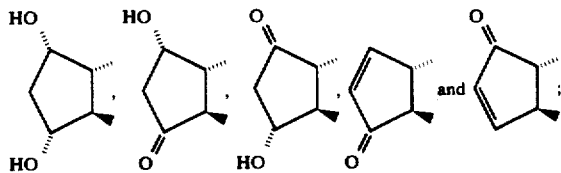

$R^1$ is hydrogen or lower alkyl;

$R^2$ is $C_6$-$C_{12}$ alkyl, $C_6$-$C_{12}$ alkenyl or $C_6$-$C_{12}$ alkadienyl or a pharmaceutically acceptable salt thereof.

The invention also relates to a kit for delivery of a topical solution for treatment of glaucoma which comprises (a) container having a solution including a compound of the formula (I), and (b) means for topical delivery of said solution to the eye in a controlled dosage.

19 Claims, No Drawings

TREATMENT FOR HYPERTENSION OR GLAUCOMA IN EYES

CROSS-REFERENCE TO RELATED APPLICATIONS

This application is a continuation-in-part application of U.S. patent application Ser. No. 07/778983 filed on Nov. 6, 1991, abandoned, the entire contents of which are hereby incorporated by reference. This application is also entitled to the benefit of PCT International Application PCT/JP91/00305.

FIELD OF THE INVENTION

The present invention relates to the use of 15-deoxy-prostaglandin derivatives for the treatment of hypertension or glaucoma in the eyes.

BACKGROUND OF THE INVENTION

Prostaglandins are a class of physiologically active substances which are derived from eicosapolyenoic acid such as arachidonic acid through biosynthetic pathway in animal tissues and have, as a fundamental chemical structure, prostanoic acid of the formula:

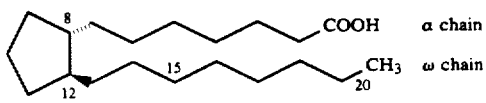

Prostaglandins are produced through biosynthesis in various tissues, and classified into several families Thus, prostaglandins are categorized into A-J groups depending on the position of oxgen atom attached to the 5 membered ring moiety and the position of a double bond in the ring moiety. Alternatively, prostaglandins can be categorized into 3 groups depending on the number of double bonds in the side chains. As a result, prostaglandins are designated as $PGA_2$, $PGE_1$, $PGF_{2\alpha}$, according to both categorizations.

Prostaglandins possess as a whole diverse bioactivities, which include, for example, vasodilator activity, platlet aggregation-inhibiting activity, uterotonic activity, gastrointestinal motility-promoting activity, etc.

Further, some prostaglandins have intraocular pressure-reducing activity. For example, Japanese Patent Publication (kokai) No. 1418/1984 describes that $PGF_{2\alpha}$ has a high intraocular pressure-reducing activity and that 15-keto-$PGF_{2\alpha}$ has the same activity although it is less potent. However, these natural prostaglandins are chemically and biologically labile, and are easily subject to metabolic degradation because they contain in the chemical structure a labile allyl alcohol moiety comprising a double bond between 13 and 14 positions and a hydroxy group at 15 position in the ω chain.

13,14-Dihydro-15-ketoprostaglandin which is a metabolic product of prostaglandins has been known as a compound which does not contain the labile moiety and has been known to be a useful compound having the intraocular pressure-reducing activity.

The inventors of the invention have found new useful compounds by screening a large amount of prostaglandin derivatives which are stable and capable of being chemically synthesized. Also, the inventors of the invention found that derivatives of conventional prostaglandins which are derived from said conventional prostaglandins by deleting the hydroxy group at 15-position are more stable, particularly in liquid phase, than the conventional prostaglandins, and that they show the intraocular pressure-reducing activity. Thus, the invention provides a new use of these derivatives. In particular, the compounds as described below have a significant intraocular pressure-reducing activity, while they do not produce any side effects such as hyperemia of conjunctiva, and initial increase in intraocular pressure which are often observed in known prostaglandins. Accordingly, the 15-deoxyprostaglandins may be a therapeutical agent useful for treating an ocular disease, in particular glaucoma, which is assumed to be caused by increased intaocular pressure.

As one embodimet, the present invention provides a method for treating hypertension or glaucoma in the eye comprising contacting the surface of the eye with a therapeutic amount of a 15-deoxyprostaglandin derivative of the formula (I):

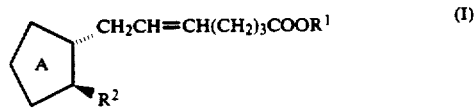

in which

is a 5 membered ring which is selected from a group consisting of

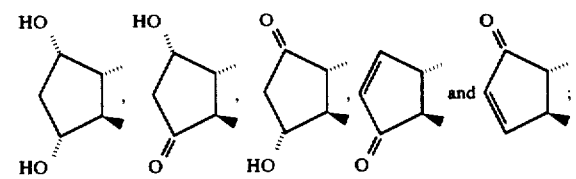

$R^1$ is hydrogen or lower alkyl;

$R^2$ is $C_6$–$C_{12}$ alkyl, $C_6$–$C_{12}$ alkenyl or $C_6$–$C_{12}$ alkadienyl or a pharmaceutically acceptable salt thereof.

The term "$C_6$–$C_{12}$ alkyl" in the definition of $R^2$ refers to hexyl, heptyl, octyl, nonyl, decyl, undecyl, dodecyl. $R^2$ may be an unsaturated haydrocarbon chain containing one or more double bonds, with $C_8$–$C_{10}$ alkenyl or $C_8$–$C_{10}$ alkadienyl being preferred. Specific examples of the unsaturated hydrocarbon chain are 1-hexenyl, 2-hexenyl, 1,3-hexadienyl, 1-heptenyl, 2-heptenyl, 1,3-heptadienyl, 1-octenyl, 2-octenyl, 1,3-octadienyl, 1-nonenyl, 2-nonenyl, 1,3-nonadienyl, 1-decenyl, 2-decenyl, 1,3-decadienyl, 1-undecenyl, 2-undecenyl, 1,3-undecadienyl, 1-dodecenyl, 2-dodecenyl, and 1,3-dodecadienyl.

15-Deoxyprostaglandin derivatives of the formula (I) include all of the stereoisomers and mixture thereof.

Preferably, 15-deoxyprostaglandin derivatives of the above formula in which

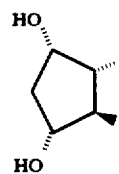 is 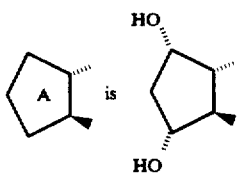

are used in the method of the present invention. More preferably, (5Z,13E,9S,11R)-9,11-dihydroxy-5,13-prostadienoic acid of the formula:

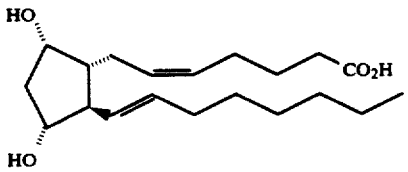

or pharmaceutically acceptable salts or lower alkyl esters is used. Among the above derivatives, a sodium salt of (5Z,13E,9S,11R)-9,11-dihydroxy-5,13-prostadienoic acid is especially preferred in the light of solubility in water.

It should be noted that (5Z,13E,9S,11R)-9,11-dihydroxy-5,13-prostadienoic acid of the formula:

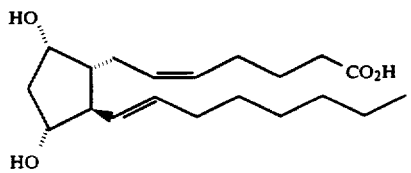

and methyl ester thereof have been described in Gorman, *Proc., Natl., Acad., Sci.*, U.S.A. 74 vol ,9,4007–4011. However, Gorman neither describes nor suggests the use of the compounds as an intraocular pressure-reducing agent.

The carboxy moiety in the above-noted compounds may be either a free carboxylic acid or a pharmaceutically acceptable salt or ester thereof. The salt may be, for example, an alkali metal salt such as a lithium salt, a sodium salt, or a potassium salt; an alkaline earth metal salt such as a calcium salt; an ammonium salt; an organic base salt such as triethylamine, 2-aminobutane, tert-butylamine, diisopropylethylamine, n-butylmethylamine, n-butyldimethylamine, tri-n-butylamine, dicyclohexylamine, N-isopropylcyclohexylamine, tromethamine, furfurylamine, benzylamine, methylbenzylamine, dibenzylamine, N,N,-dimethylbenzylamine, 2-chlorobenzylamine, 4-methoxybenzylamine, 1-naphthylmethylamine, diphenylbenzylamine, triphenylamine, 1-naphtylamine, 1-aminoanthracene, 2-aminoanthracene, dehydroabietylamine, N-methylmorpholine or pyridine; an amino acid salt such as a lysine or arginine salt. Examples of the ester are a lower alkyl ester, for example, methyl, ethyl, propyl, isopropyl, butyl, isobutyl, tert-butyl or pentyl ester. The lower alkyl ester moiety may be substituted with an optional group.

In the method of the present invention, the dose of the compounds of the formula (I) varys depending on purpose of the treatment and effect, method for administration, a particular compound used in the treatment, or age and body weight of a particular patient. Typically, in the case of oral administration, the dose is about 200 μg/kg/day–about 20 mg/kg/day, preferablly about 1 mg/kg/day–about 10 mg/kg/day, but not limited to them. In the case of ophthalmic application for treating hypertension and glaucoma in the eyes, the dose is about 0.01 μg/eye/day–about 1000 μg/eye/day, preferablly about 0.1 μg/eye/day–about 200 μg/eye/day. When the compoumd of (5Z,13E,9S,11R)-9,11-dihydroxy-5,13- prostadienoic acid of the formula:

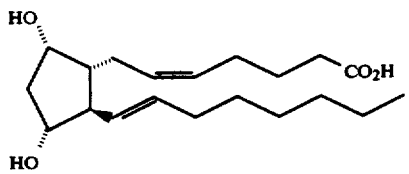

or pharmaceutically acceptable salts or lower alkyl esters is used in the method, the preferred dose of the compound is 1 μg/eye/day–about 1000 μg/eye/day, and the more preferred dose is about 5 μg/eye/day–about 500 μg/eye/day.

The above dose which can be used in the method of the present invention may be divided into 1–5 portions in application. Accordingly, the present invention also relates to the method for treating hypertension or glaucoma in the eye comprising periodically, contacting the compounds of the formula (I) with the surface of the eye.

As another embodiment, the invention provides a kit for delivery of a solution for topical treatment of glaucoma which comprises:

(a) container having a solution including a compound of the formula (I), and
(b) means for topical delivery of said solution to the eye in a controlled dosage.

Preferred kit is of the compound which is (5Z,13E,9S,11R)-9,11-dihydroxy-5,13-prostadienoic acid of the formula:

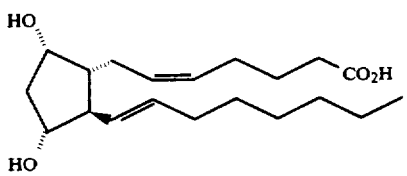

or pharmaceutically acceptable salts or lower alkyl esters.

The compounds used in the method of the invention can be prepared by the following process:

A lactone of the formula (IV):

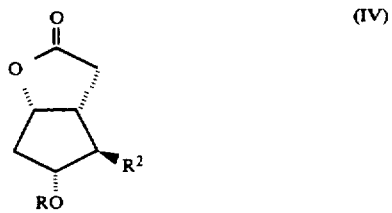

(IV)

in which R is hydroxy-protecting group, $R^2$ is the same meaning as defined above is reduced with a metal hydride to form a lactol of the formula (III):

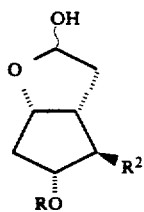

in which R and R² are the same meaning as above.

The resultant lactol (III) is then reacted with an ylide in the condition of Wittig reaction to yield the compound of the formula (II):

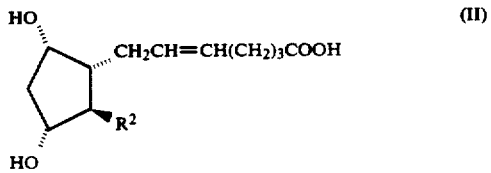

in which R and R² are the same meaning as above.

Following deprotection and optional esterification or salification of the compound, 15-deoxyprostaglandin derivatives of the type of $PGF_{2\alpha}$ can be obtained. The hydroxy-protecting group may be selected from various protecting groups which are described in Protective Groups in Organic Synthesis, T. W. Greene, John Wiley & Sons, Inc., New York, p. 10, 1981. Examples of the protecting group are those forming an alkyl ether, such as methyl, methoxymethyl, methylthiomethyl, 2-methoxyethoxyethyl, tetrahydropyranyl, 1-ethoxyethyl, benzyl, and p-methoxybenzyl; those forming a silyl ether, such as triethylsilyl, t-butyldimethylsilyl, and t-butyldiphenylsilyl; those forming an ester, such as acetyl, benzoyl, p-methylbenzoyl, and o-methoxybenzoyl.

The lactone (IV) as a starting material, is prepared from the aldehyde analogue which is obtained by oxidizing commercially available Corey lactone, using the process described below:

(i) Synthesis of compounds (IV) wherein R² is 1-alkenyl

The compounds (IV) can be prepared by reacting the above-noted aldehyde and an ylide prepared from an alkyltriphenylphosphonium halide in the condition of Wittig reaction. If desired, cis-trans isomerization reaction may be conducted on the resultant compounds.

(ii) Synthesis of compounds (IV) wherein R² is alkyl

The compounds (IV) can be prepared by catalytic reduction of the lactone (IV) obtained in the above process (i).

(iii) Synthesis of compounds (IV) wherein R² is unsaturated alkyl other than 1-alkenyl.

The above aldehyde is reacted with a formylalkylene-triphenylphosphorane or an ylide obtainable from an alkyltriphenylphosphonium halide having a protected hydroxy in the condition of Wittig reaction If desired, catalytic reduction or cis-trans isomerization reaction can be conducted.

In the case that the ylide having a protected hydroxy is used, deprotection and oxidation are carried out to form formyl compounds. A desired compound (IV) can be prepared by treating the resultant aldehyde thus obtained according to the process (i).

15-Deoxyprostaglandin derivatives of the type of $PGD_2$, $PGE_2$, $PGJ_2$ or $PGA_2$ can be prepared by using the derivatives of the type of $PGF_{2\alpha}$ as a starting material. The outline of the process is shown in the scheme shown below. The details are illustrated in the working examples hereinafter described.

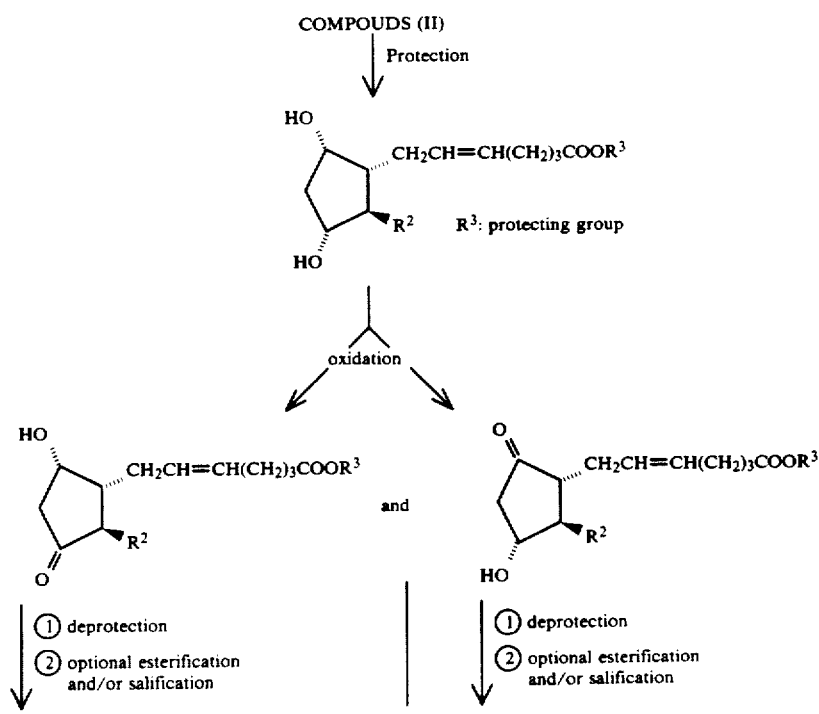

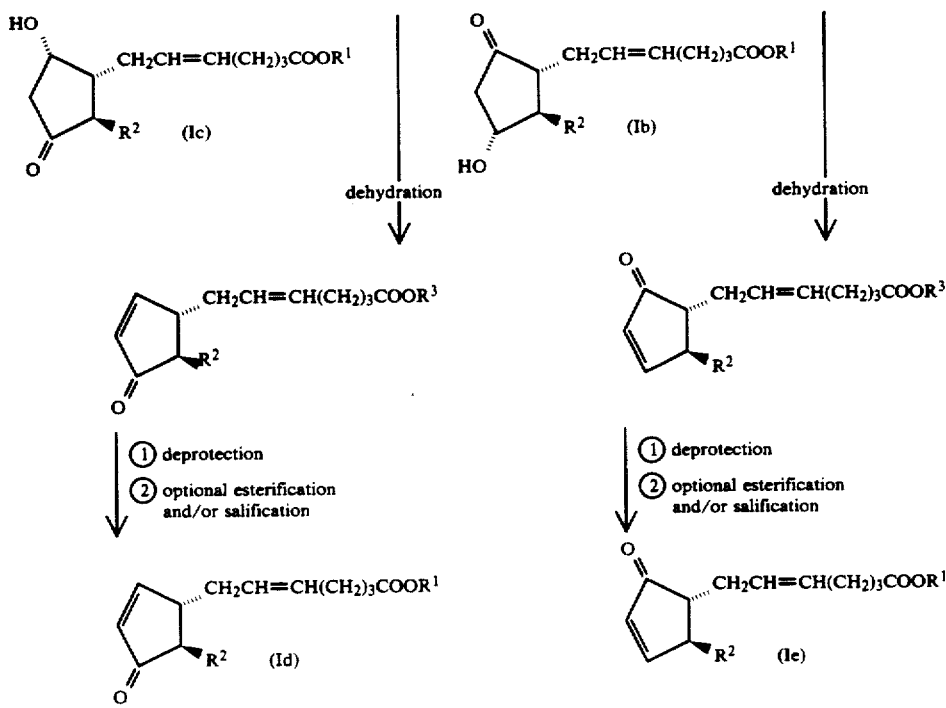

The 15-deoxyprostaglandin derivatives of the invention can be administered topically or systemically using known procedures for administration. The derivatives of the invention can be formulated into a dosage form which is suitable for oral, intraarterial, intravenous, intracutaneous, intramuscular, intrarectal, or ophthalmic administration.

Recently, the inventors have found that the compounds in which the carboxy moiety is a lower alkyl ester are preferred in terms of pharmacological activity. However, esterification of the carboxylic acid results in decrease of water-solubility. Accordingly, in preparing a formulation for use as an eye drop, the compound in the form of an ester is preferably formulated into an oily formulation, or the solubility of the compound may be improved either by addition of any surfactant to the formulation or introduction of any hydrophilic group (for example hydroxy or lower alkoxy such as methoxy) into the ester moiety of the compound.

The dose of the compounds of the invention varys depending on purpose of the treatment and effect, method for administration, or age and body weight of a particular patient. Typically, in the case of oral administration, the dose is about 200 μg/kg/day–about 20 mg/kg/day, preferablly about 1 mg/kg/day–about 10 mg/kg/day, but not limited to them. In the case of ophthalmic application for treating glaucoma, the dose is about 0.01 μg–about 1000 μg/eye/day, preferablly about 0.1 μg–about 200 μg/eye/day, and this dose may be divided into 1–5 portions in application.

EXAMPLES

The following detailed examples are presented by way of illustration of certain specific embodiments of the invention. The examples are representative only and should not be construed as limiting the invention in any respect.

EXAMPLE 1

Preparation of (1S,6R,7R)-2-oxa-3-oxo-6-[(1Z)-octenyl]-7-tetrahydropyranyloxy-cis-bicyclo[3.3.0]octane (compound 2)

Heptyltriphenylphosphonium bromide (3.78 g, 8.58 mmole) was suspended in tetrahydrofuran (23 ml), and potassium tert-butoxide (0.873 g, 7.79 mmole) was added thereto under ice-cooling. The mixture was stirred at the same temperature for 10 minutes. The dark orange mixture thus obtained was cooled to −78° C. and 10 ml of a solution of (1S,6R,7R)-2-oxa-3-oxo-6-formyl-7-tetrahydropyranyloxy-cis-bicyclo[3.3.0]-octane (compound 1) (0.99 g, 3.89 mmole) in tetrahydrofuran, which had been prepared from Corey lactone according to E. J. Corey, H. Shirahama, H. Yamamoto, S. Terashima, A. Venkateswarlu and T. K. Schaaf, J. Am. Chem.Soc., 93, 1490 (1971), was added thereto. The ice bath was removed, and the reaction mixture was allowed to warm up to room temparature over 30 minutes while stirring. After stirred for additional one hour at room temparature, an aqueous solution of ammonium chloride was added. The mixture was concentrated in vacuo, and the residue was extracted with ether-ethyl acetate (2:1). The extract was washed with diluted hydrochloric acid, aqueous sodium bicarbonate and brine successively and then dried over anhydrous magnescium sulfate, and the solvent was evaporated off. The resultant brown semi-solid material (3.1 g) was chromatographed over silica gel (39 g), eluting with 1:7–1:3 of ethyl acetate:n-hexane, to yield 600 mg of a crude product. The product was purified with Lobar column (ethyl acetate:n-hexane=1:3) to yield 484 mg of the title compound 2 as a colorless oil (yield 37%).

NMR (CDCl$_3$); δ0.88 (t, J=7Hz, 3H), 1.1–3.05 (m, 22H), 3.50 (m, 1H), 3.8–4.1 (m, 2H), 4.67 (m, 1H), 5.05 (m, 2H), 5.50 (m, 1H).

IR (CHCl$_3$); 1765 cm$^{-1}$.

EXAMPLE 2

Preparation of
(1S,6R,7R)-2-oxa-3-oxo-6-[(1E)-ocetnyl]-7-tetrahydropyranyloxy-cis-bicyclo[3.3.0]octane (compound 3)

The compound 2 obtained in Example 1 (336 mg, 1 mmole) was dissolved in benzene (15 ml), and 5-mercapto-1-methyltetrazole disulfide (115 mg, 0.5 mmole) and α,α'-azobis-isobutyronitrile (16 mg, 0.1 mmole) were added thereto, and the mixture was refluxed with stirring for 10 hours. The reaction mixture was washed with aqueous sodium carbonate and then with brine, and dried over anhydrous sodium sulfate, and the solvent was evaporated off. The resultant colorless oil (400 mg) was chromatographed over silica gel (10 g), eluting with 1:7-1:5 of ethyl acetate:n-hexane, to yield a curde product (260 mg). The product was further purified with Lobar column (ethyl acetate:n-hexane=1:3) to yield 202 mg of the title compound 3 as a colorless oil (yield 60%).

NMR (CDCl$_3$); δ0.88 (t, J=7Hz, 3H), 1.1-2.8 (m, 22H), 3.50 (m, 1H), 3.7-4.2 (m, 2H), 4.68 (m, 1H), 4.95 (m, 1H), 5.25 (m, 1H), 5.50 (m, 1H).

IR (CHCl$_3$); 1765 cm$^{-1}$.

EXAMPLE 3

Preparation of
(5Z,13E,9S,11R)-9-hydroxy-11-tetrahydropyranyloxy-5,13-prostadienoic acid (compound 5)

The compound 3 obtained above (336 mg, 1 mmole) was dissolved in toluene (12 ml), and 1M diisobutyl aluminum hydride in toluene (1.1 ml, 1.1 mmole) was added thereto at −78° C. The solution was stirred at the same temperature for one hour, and then aqueous ammonium chloride was added thereto, and the temperature was allowed to warm to room temperature. The reaction mixture was extracted with ethyl acetate, and the extract was washed with brine and dried over anhydrous sodium sulfate, and then the solvent was evaporated off. The residue (340 mg) was chromatographed over silica gel (3.4 g), eluting with 1:2 of ethyl acetate:n-hexane, to yield lactol 4 (314 mg, 93%) as a colorless oil.
IR (CHCl$_3$); 3610, 3390 cm$^{-1}$.

After 4-carboxybutyltriphenylphosphonium bromide (1.219 g, 2.76 mmole) was suspended in tetrahydrofuran (15 ml), a potassium tert-butoxide (680 mg, 6.07 mmole) was added thereto under ice cooling, and the mixture was stirred at the same temperature for 10 minutes. The resultant red mixture was cooled to −30° C., and 6 ml of a solution of the lactol 4 obtained above (310 mg, 0.92 mmole) in tetrahydrofuran was added thereto. After removing the cooling bath, the reaction mixture was allowed to warm to room temperature with stirring, and stirred for additional one hour. To the resultant yellow mixture was added a solution of ammonium chloride in water, and the mixture was concentrated in vacuo. An ice water was added to the residue, and the mixture was acidified with diluted hydrochloric acid to pH 4-5 under cooling, and extracted with ethyl acetate. The ethyl acetate layer was extracted with aqueous sodium carbonate, and the water phase was acidified again to pH 4-5, and then extracted with a mixture of methylene chloride and ethyl acetate (2:1). After the extract was dried over anhydrous magnesium sulfate, the solvent was evaporated off to yield 790 mg of a semicrystalline product. To the product was added ethyl ether, and the dissolved portion gas filtered and the solvent was evaporated off to yield 288 mg of a crude product. The product was chromatographed over silicic acid (8.6 g), eluting with 1:10-1:3 of ethyl acetate:n-hexane, to yield 234 mg of the title compound as a colorless oil (yield 60%).

NMR (CDCl$_3$); δ0.88 (t, J=7Hz, 3H), 1.2-2.5 (m, 30H), 3.45 (m, 1H), 3.85 (m, 1H), 4.07 (m, 2H), 4.69 (m, 1H), 5.2-5.6 (m, 4H).

IR (CHCl$_3$); 3500, 2700-2400 (broad), 1705 cm$^{-1}$.

EXAMPLE 4

Preparation of
(5Z,13E,9S,11R)-9,11-dihydroxy-5,13-prostadienoic acid (compound 6)

The compound 5 obtained above (205 mg, 0.485 mmole) was dissolved in 4 ml of a mixture of acetic acid, water, and tetrahydrofuran (65:35:10). The mixture was stirred under heating at 40°-45° C. for one and half hours, and then evaporated to dryness in vacuo. The residue (184 mg) was chromatographed over silicic acid (5.5 g), eluting with 1:5-1:1 of ethyl acetate:n-hexane, to yield 149 mg of the title compound 6 as a colorless oil (yield 91%).

NMR (CDCl$_3$); δ0.88 (t, J=7Hz,3H), 1.2-2.5 (m, 22H), 3.94 (m, 1H), 4.17 (m, 1H), 1.0-4.8 (broad ,3H), 5.2-5.6 (m, 4H).

IR (CHCl$_3$); 3400, 2700-2400(broad), 1705 cm$^{-1}$.

EXAMPLE 5

Preparation of
(5Z,13E,9S,11R)-9,11-dihydroxy-5,13-prostadienoic acid metyl ester (compound 7)

The compound 6 obtained obove (104 mg, 0.307 mmole) was dissolved in acetonitrile (5 ml), and 1,8-diazabicyclo[5.4.0]-7-undecene (70 μl, 0.46 mmole) was added thereto. The mixture was stirred at room temperature for 15 minuites. Then, methyl iodide (0.19 ml, 3 mmole) was added thereto and the mixture was stirred at room temperature for five hours, and then concentrated in vacuo. To the residue was added water, and the mixture was extracted with ethyl acetate. The extract was washed successively with diluted hydrochloric acid, aqueous sodium sulfite, and brine, and then dried over anhydrous magnesium sulfate. After the solvent was evaporated off, 113 mg portion of the residue was purified with Lobar colum (ethyl acetate:n-hexane=1:1), to yield 103 mg of the title compound 7 as a colorless oil (yield 95%).

NMR (CDCl$_3$); δ0.88(t, J=7Hz, 3H), 1.2-2.4 (m, 24H), 3.67 (s, 3H), 3.92 (m, 1H), 4.17 (m, 1H), 5.18-5.61 (m, 4H).

IR (CHCl$_3$); 3450, 1720cm$^{-1}$.

EXAMPLE 6

Preparation of
(5Z,13E,9S,11R)-9,11-dihydroxy-5,13-prostadienoic acid isopropyl ester (compound 8)

The title compound 8 was obtained as a colorless oil (36 mg, 95%), following a procedure similar to that disclosed in Example 5 except that the compound 6 obtained above (33 mg, 0.1 mmole) was dissolved in acetonitrile (1 ml), and 1,8-diazabicyclo[5.4.0]-7-undecene (40 μl , 0.3 mmole) and then isopropyl iodide (0.19 μl, 1 mmole) were added thereto.

NMR (CDCl$_3$); δ0.88 (t, J=7Hz, 3H), 1.22 (d, J=6Hz, 6H), 1.25-2.35 (m, 24H), 3 92 (m, 1H), 4.17 (m, 1H), 5.00 (sept, J=6Hz, 1H), 5.18-5.60 (m,4H).

IR (CHCl$_3$); 3450, 1720 cm$^{-1}$.

EXAMPLE 7

Test for demonstrating stability of the compound 6 [The formation of (5Z,13E,9S,11R)-9,11-dihydroxy-5,13-prostadienoic acid (compound 6)]

The compound 7 obtained above (73 mg, 0.207 mmole) was dissolved in 2 ml of methanol. One ml of 1N aqueous pottasium hydroxide solution was added thereto, and the mixture was refluxed with stirring for one hour. After concentrating the solution to remove the methanol, the residue was dissolved in water and washed with ethyl acetate. The aqueous solution was acidified with adding diluted hydrochloric acid under cooling and extracted with ethyl acetate. The extract was washed with brine, and dried over anhydrous magnesium sulfate. Then, the solvent was evaporated off to give 70 mg of a crude product. The product was chromatographed over silicic acid (2 g), eluting with 1:1 of ethyl acetate:n-hexane, to give the title compound (68 mg, 97%) as a colorless oil.

The above reaction is illustrated in the following scheme.

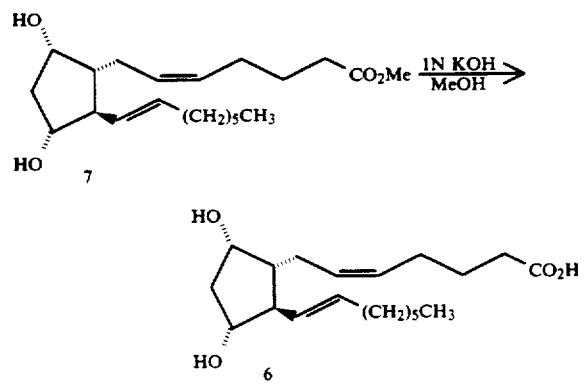

EXAMPLE 8

Preparation of (1S,6R,7R)-2-oxa-3-oxo-6-[(1Z)-decenyl]-7-tetrahydropyranyloxy-cis-bicyclo[3.3.0]octane (compound 2')

Nonyltriphenylphosphonium bromide (3.85 g, 8.20 mmole) was suspended in 25 ml of tetrahydrofuran, and 0.836 g (7.46 mmole) of potassium tert-butoxide was added, and the mixture was stirred at the same temperature for 10 minutes. The deep orange mixture thus obtained was cooled to −78° C., and 10 ml of a solution of the compound 1 obtained above (0.95 g, 3.74 mmole) in tetrahydrofuran was added thereto. Then, the reaction mixture was treated following a procedure similar to that discolsed in Example 1, to yield the title compound 2' (573 mg, 42%) as a colorless oil.

NMR (CDCl$_3$); δ0.88 (t, J=7Hz, 3H), 1.1–3.05 (m, 26H), 3.50 (m, 1H), 3.8–4.1 (m, 2H), 4.68 (m, 1H), 5.05 (m, 2H), 5.50 (m, 1H).

IR (CHCl$_3$); 1765 cm$^{-1}$.

EXAMPLE 9

Preparation of (1S,6R,7R)-2-oxa-3-oxo-6-[(1E)-decenyl]-7-tetrahydropyranyloxy-cis-bicyclo[3.3.0]octane (compound 3')

The compounds 2' obtained above (566 mg, 1.55 mmole) was dissolved in 30 ml of benzene, and 5-mercapto-1-methyltetrazole disulfide (180 mg, 0.78 mmole) and α,α'-azobis-isobutyronitrile (25 mg, 0.15 mmole) were added thereto, and the mixture was refluxed with stirring for 2.5 hours. Then, the reaction mixture was treated following a procedure similar to that of Example 2, to yield the compound 3' (383 mg, 67%) as a colorless oil.

NMR (CDCl$_3$); δ0.88(t, J=7Hz, 3H), 1.1–2.85 (m, 26H), 3.50 (m, 1H), 3.75–4.15 (m, 2H), 4.68 (m, 1H), 4.97 (m, 1H), 5.25 (m, 1H), 5.50 (m, 1H).

IR (CHCl$_3$); 1765cm$^{-1}$.

EXAMPLE 10

Preparation of (5Z,13E,9S,11R)-20-ethyl-9-hydroxy-11-tetrahydropyranyloxy-5,13-prostadienoic acid (compound 5')

The compound 3' obtained above (398 mg, 1.09 mmole) was dissolved in 14 ml of toluene, and 1.2 ml of 1M solution of diisobutyl aluminum hydride (1.2 mmole) in toluene was added thereto at −78° C. Then, the reaction mixture was treated following the procedure similar to that of Example 3, to yield the compound 4' (395 mg, 98%) as a colorless oil.

IR (CHCl$_3$); 3600, 3390 cm$^{-1}$.

4-Carboxybutyltriphenylphosphonium bromide (1.409 g, 3.18 mmole) was suspended in tetrahydrofuran (15 ml), and potassium tert-butoxide (780 mg, 6.99 mmole) was added under ice-cooling, and the mixture was stirred at the same temperature for 10 minutes. The red mixture thus obtained was cooled to −30° C., and to the mixture was added 10 ml of a solution of the lactol compound 4' obtained above (388 mg, 1.06 mmole) in tetrahydrofuran. Then, the reaction mixture was treated following the procedure similar to that of Example 3, to yield the title compound 5' (304 mg, 64%) as a colorless oil.

NMR (CDC$_{13}$); δ0.88(t, J=7Hz, 3H), 1.1–2.5 (m, 34H), 3.45 (m, 1H), 3.85 (m, 1H), 4.07 (m, 2H), 4.70 (m, 1H), 5.2 −5.6 (m, 4H).

IR (CHCl$_3$); 3512, 2700–2400 (broad), 1708 cm$^{-1}$.

EXAMPLE 11

Preparation of (5Z,13E,9S,11R)-20-ethyl-9,11-dihydroxy-5,13-prostadienoic acid (compound 6')

The compound 5' obtained above (297 mg, 0.66 mmole) was dissolved in 6 ml of a mixture of acetic acid, water, and tetrahydrofuran (65:35:10), and the solution was heated with stirring at 40°–45° C. for two hours. Then, the reaction mixture was treated following the procedure similar to that of Example 4, to yield the title compound 6' (194 mg, 80%) as a colorless oil.

NMR (CDCl$_3$); δ0.88 (t, J=7Hz, 3H), 1.2–2.4 (m, 26H), 3.93 (m, 1H), 4.18 (m, 1H), 3.4–4.5 (broad, 3H), 5.15–5.60 (m, 4H).

IR (CHCl$_3$); 3400, 2700–2400 (broad), 1705 cm$^{-1}$.

EXAMPLE 12

Preparation of (5Z,13E,9S,11R)-20-ethyl-9,11-dihydroxy-5,13-prostadienoic acid isopropyl ester (compound 8')

The compound 6 obtained above (37 mg, 0.1 mmole) was dissolved in acetonitrile (1 ml), and 1,8-diazabicyclo[5.4.0]-7-undecene (75 μl, 0.5 mmole) and isopropyl iodide (0.29ml, 3mmole) were successively added thereto. Then, the reaction mixture was treated following the procedure similar to that of Example 5, to yield the title compound 8' (35 mg, 85%) as a colorless oil.

NMR (CDCl₃); δ0.88 (t, J=7Hz, 3H), 1.22 (d, J=6Hz, 6H), 1.25-2.40 (m, 28H), 3.92 (m, 1H), 4.18 (m, 1H), 5.01 (sept, J=6Hz, 1H), 5.15-5.60 [m,4H).

IR (CHCl₃); 3500, 1715 cm⁻¹.

The comprehensive scheme illustrating the reactions described in Examples 1-12 is shown below.

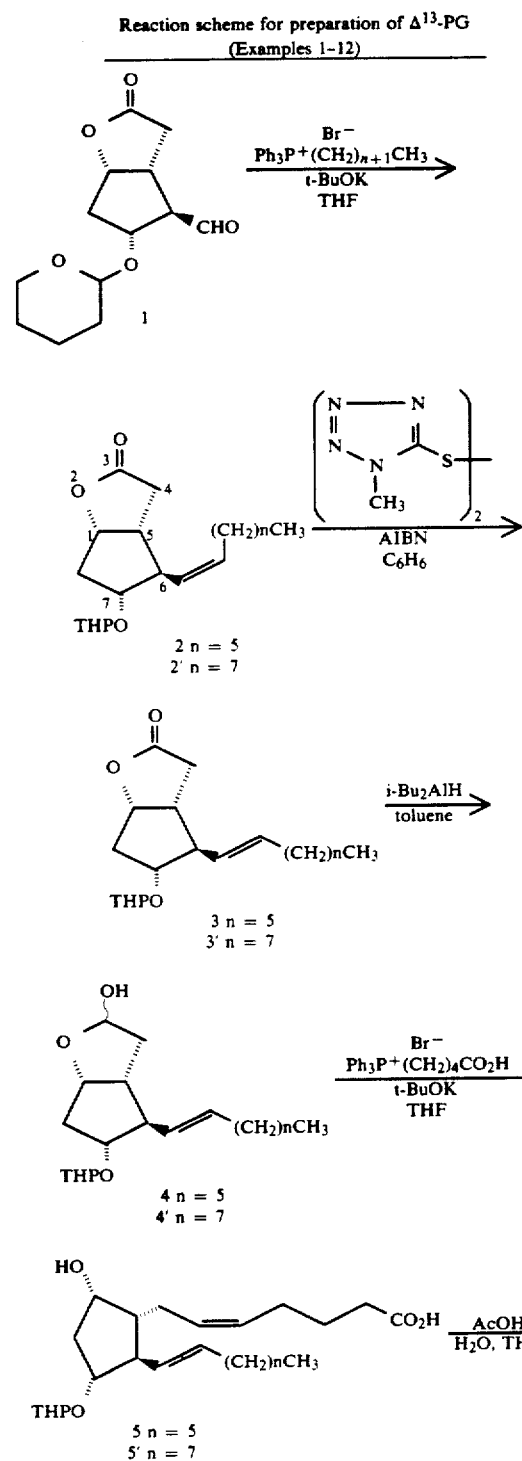

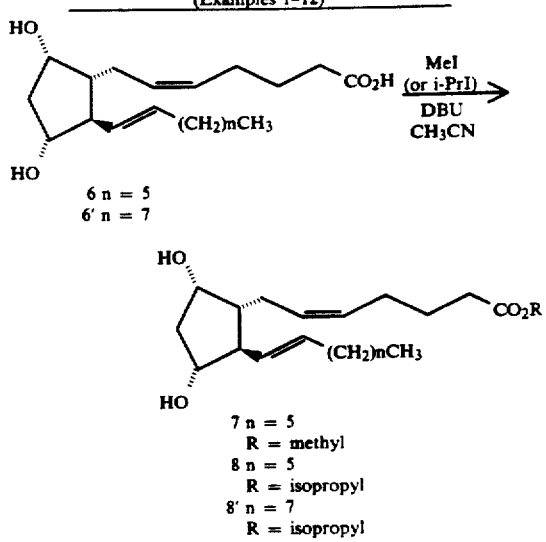

EXAMPLE 13

Preparation of (1S,6R,7R)-2-oxa-3-oxo-6-octyl-7-tetrahydropyranyloxy-cis-bicyclo[3.3.0]octane (compound 9)

The compound 2 obtained above (405 mg, 1.20 mmole) was dissolved in methanol (10 ml), and 5% paladium-carbon (80 mg) was added thereto, and the mixture was stirred under hydrogen at one atmospheric pressure for one hour. After the mixture was filtered and the filtrate was evaporated, the residue (405 mg) was chromatographed over silica gel (4 g), eluting with 1:10-1:3 of ethyl acetate : n-hexane, to yield the title compound 9 (393 mg, 97%) as a colorless oil.

NMR (CDCl₃); δ0.88 (t, J=7Hz, 3H), 1.1-2.9 (m, 26H), 3.50 (m, 1H), 3.75-4.15 (m, 2H), 4.66 (m, 1H), 5.01 (m, 1H).

IR (CHCl₃); 1764 cm⁻¹.

EXAMPLE 14

Preparation of (5Z,9S,11R)-9-hydroxy-11-tetrahydropyranyloxy-5-prostenoic acid (compound 11)

The compound 9 obtained above (378 mg, 1.12 mmole) was dissolved in toluene (12 ml), and 1M solution of diisobutyl aluminum hydride in toluene (1.23 ml, 1.23 mmole) was added thereto at −78° C. Then, the reaction mixture was treated following the procedure similar to that of Example 3, to yield lactol 10 (370 mg, 97%) as a colorless oil.

IR (CHCl₃); 3594, 3384 cm⁻¹.

4-Carboxybutyltriphenylphosphonium bromide (1.427 g, 3.21 mmole) was suspended in tetrahydrofuran (15 ml), and potassium tert-butoxide (794 mg, 7.06 mmole) was added thereto under ice cooling, and the mixture was stirred at the same temperature for 10 minutes. The red mixture thus obtained was cooled to −30° C., and to the mixture was added 7 ml of a solution of the lactol 10 obtained above (365 mg, 1.07 mmole) in tetrahydrofuran. Then, the reaction mixture was treated following the procedure similar to that of Example 3, to yield the title compound 11 (317 mg, 70%) as a colorless oil.

NMR (CDCl3); δ0.88 (t, J=7Hz, 3H), 1.1–2.45 (m, 34H), 3.50 (m, 1H), 3.85 (m, 1H), 4.06 (m, 2H), 4.69 (m, 1H), 5.3–5.6 (m, 2H).

IR (CHC3); 3512, 2700–2400 (broad), 1708 cm$^{-1}$.

EXAMPLE 15

Preparation of (5Z,9S,11R)-9,11-dihydroxy-5-prostenoic acid 12

The compound 11 obtained above (220 mg, 0.518 mmole) was dissolved in 4 ml of a mixture of acetic acid-water-tetrahydrofuran (65:35:10) and the solution was heated with stirring at 40°–45° C. for one and half hours. Then, the reaction mixture was treated following the procedure similar to that of Example 4, to yield the title compound 12 (156 mg, 88%) as a colorless oil.

NMR (CDCl3); δ0.88 (t, J=7Hz, 3H), 1.1–2.45 (m, 26H), 3.96 (m, 1H), 4.18 (m, 1H), 3.6–4.9 (broad, 3H), 5.3–5.6 (m,2H).

IR (CHCl3); 3664, 3432, 2700–2400 (broad), 1707 cm$^{-1}$.

EXAMPLE 16

Preparation of (5Z,9S,11R)-9,11-dihydroxy-5-prostenoic acid isopropyl ester (compound 13)

The compound 12 obtained above (80 mg, 0.235 mmole) was dissolved in acetonitrile (3 ml), and 1,8-diazabicyclo[5.4.0]-7-undecene (0.21 ml, 1.4 mmole) and then isopropyl iodide (0.69 ml, 7.0 mmole) were added thereto. Then, the reaction mixture was treated following the procedure similar to that of Example 5, to yield the title compound 13 (82 mg, 91%) as a colorless oil.

NMR (CDC13); δ0.88 (t, J=7Hz, 3H), 1.22 (d, J=6Hz, 6H), 1.2–2.45 (m, 28H), 3.95 (m, 1H), 4.18 (m, 1H), 5.01 (sept, J=6Hz, 1H), 5.3–5.6 (m, 2H).

IR (CHCl3); 3512, 1716 cm$^{-1}$.

The comprehensive scheme illustrating the reactions described in Examples 13–16 is shown below.

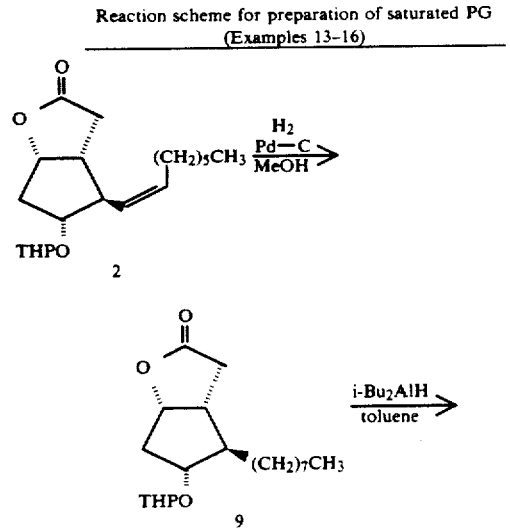

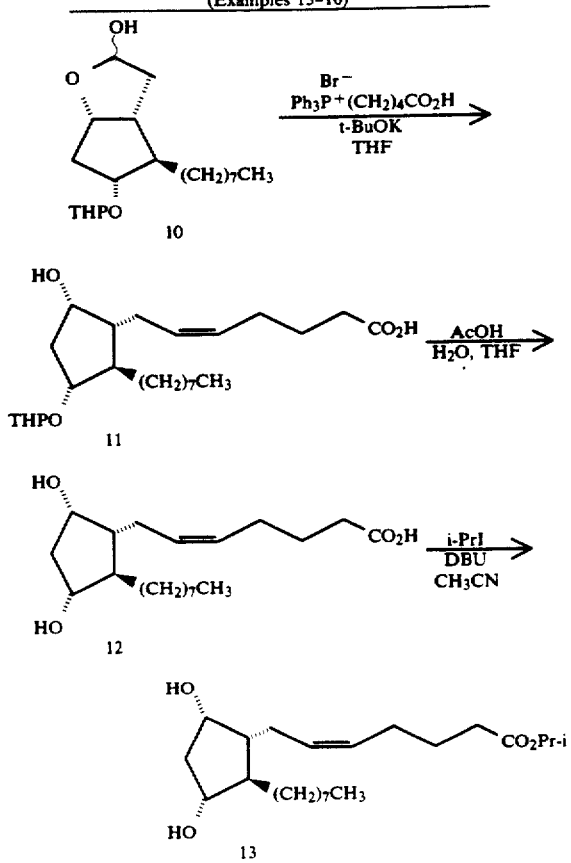

EXAMPLE 17

Preparation of (1S,6R,7R)-2-oxa-3-oxo-6-[7-tert-butyldimethyl-silyloxy-(1Z)-heptenyl]-7-tetrahydropyranyloxy-cis-bicyclo[3.3.0]octane (compound 14)

After (6-tert-butyldimethylsilyloxyhexyl)triphenyl-phosphonium bromide (2.56 g, 4.59 mmole) was dissolved in tetrahydrofuran (26 ml), potassium tert-butoxide (467 mg, 4.17 mmole was added thereto under ice-cooling, and the mixture was stirred at the same temperature for 10 minutes. The deep orange mixture thus obtained was cooled to −78° C., and 6 ml of solution of the compound 1 obtained above (530 mg, 2.08 mmole) in tetrahydrofuran was added thereto. Then, the reaction mixture was treated following the procedure similar to that of Example 1, to yield the title compound 14 (520 mg, 55%) as a colorless oil.

NMR (CDCl3); δ0.05 (s, 6H), 0.89 (s, 9H), 1.2–3.0 (m, 20H), 3.48 (m, 1H), 3.60 (t, J=7Hz, 2H), 3.76–4.07 (m, 2H), 4.68 (m, 1H), 4.9–5.15 (m, 2H), 5.48 (m, 1H).

IR (CHCl3); 1765 cm$^{-1}$.

EXAMPLE 18

Preparation of (1S,6R,7R)-2-oxa-3-oxo-6-(7-tert-butyldimethylsilyloxyheptyl)-7-tetrahydropyranyloxy-cis-bicyclo[3.3.0]octane (compound 15)

The compound 14 obtained above (335 mg, 0.741 mmole) was dissolved in methanol (10 ml), and 5% palladium-carbon (67 mg) was added thereto, and the mixture was stirred under one hydrogen at atmospheric pressure for one hour. The mixture was filtered, and the filtrate was evaporated to yield the title compound 15 (320 mg, 97%) as a colorless oil.

NMR (CDCl$_3$); δ0.05 (s, 6H), 0.89 (s, 9H), 1.2–2.9 (m, 24H), 3.49 (m, 1H), 3.60 (t, J=7Hz, 2H), 3.75–4.15 (m, 2H), 4.65 (m, 1H), 5.01 (m, 1H).

IR (CHCl$_3$); 1764 cm$^{-1}$.

EXAMPLE 19

Preparation of (1S,6R,7R)-2-oxa-3-oxo-6-(7-hydroxyheptyl)-7-tetrahydropyranyloxy-cis-bicyclo[3.3.0]octane (compound 16)

The compound 15 obtainer above (320 mg, 0.704 mmole) was dissolved in tetrahydrofuran (4 ml), and 1M solution of tetrabutylammonium fluoride in tetrahydrofuran (0.845 ml, 0.845 mmole) was added thereto at room temperature, and the mixture was stirred for three hours. After adding acetic acid (40 μl, 0.668 mmole) thereto under cooling, the reaction mixture was evaporated to dryness. The residue was chromatographed over silica gel (7.2 g), eluting with 1:3–1:2 of ethyl acetate:n-hexane, to yield the title compound 16 (224 mg, 93%) as a colorless oil.

NMR (CDCl$_3$); δ1.1–2.9 (25H), 3.50 (m, 1H), 3.64 (t, J=7Hz, 2H), 4.65 (m, 1H), 5.01 (m, 1H).

IR (CHCl$_3$); 3622, 3468, 1764 cm$^{-1}$.

EXAMPLE 20

Preparation of (1S,6R,7R)-2-oxa-3-oxo-6-(6-formylhexyl)-7-tetrahydropyranylo>.y-cis-bicyclo[3.3.0]octane (compound 17)

Thirty five μl (0.4 mmole) of oxalyl chloride was dissolved in methylene chloride (1 ml), and 1 ml of a solution of dimethylsulfoxide (57 μl, 0.8 mmole) in methylene chloride was added thereto at −60° C., and the mixture was stirred at the same temperature for 10 minutes. Two ml of a solution of the compound 16 obtained above (68 mg, 0.2 mmole) in methylene chloride and 0.11 ml of triethylamine (0.8 mmole) were successively added thereto, and then the cooling bath was removed. The reaction was allowed to warm to 0° C., and water was added to the resultant white suspension, and the mixture was extracted with methylene chloride. The extract was washed with diluted hydrochloric acid, aqueous sodium bicarbonate and brine successively, and dried over sodium sulfate. Then, the solvent was evaporated off to yield the title compound 17 (68 mg, quantitative) as a colorless oil.

NMR (CDCl$_3$); δ1.1–2.9 (m, 24H), 3.50 (m, 1H), 3.75–4.15 (m, 2H), 4.64 (m, 1H), 5.01 (m, 1H), 9.77 (t, J=2Hz, 1H).

IR (CHCl$_3$); 2726, 1764, 1720 cm$^{-1}$.

EXAMPLE 21

Preparation of (1S,6R,7R)-2-oxa-3-oxo-6-(7-octenyl)-7-tetrahydropyranyloxy-c-s-bicyclo[3.3.0]octane (compound 18)

Methyltriphenylphosphonium bromide (642 mg, 1.79 mmole) was suspended in tetrahydrofuran (4 ml), and 1.6M n-buthyl lithium-hexane solution (1.0 ml, 1.6 mmole) was added thereto under ice cooling, and the mixture was stirred at the same temperature for 10 minutes. The yellow mixture thus obtained was cooled to −78° C., and to the mixture was added 2 ml of a solution of the compound 17 obtained above (66 mg, 0.195 mmole) in tetrahydrofuran. Then, the reaction mixture was treated following the procedure similar to that of Example 1, to yield the title compound 18 (24 mg, 37%) as a colorless oil.

NMR (CDCl$_3$); δ1.1–3.05 (m, 24H), 3.50 (m, 1H), 3.75–4.17 (m, 2H), 4.64 (m, 1H), 4.87–5.10 (m, 3H), 5.80 (m, 1H).

IR (CHCl$_3$); 1761, 1639 cm$^{-1}$.

EXAMPLE 22

Preparation of (5Z,9S,11R)-9-hydroxy-11-tetrahydropyranyloxy-5,19-prostadienoic acid (compound 20)

The compound 18 obtained above (62 mg, 0.184 mmole) was dissolved in toluene (2 ml), and 1M solution of diisobutyl aluminum hydride in toluene (0.20 ml, 0.20 mmole) was added thereto at −78° C. Then, the reaction mixture was treated following the procedure similar to that of Example 3, to yield lactol 19 (50 mg, 80%) as a colorless oil.

IR (CHCl$_3$); 3590, 3380, 1640 cm$^{-1}$.

4-Carboxybuthyltriphenylphosphonium bromide (196 mg, 0.442 mmole) was suspended in tetrahydrofuran (2 ml), and potassium tert-butoxide (99 mg, 0.884 mmole) was added thereto under ice cooling, and the mixture was stirred for 10 minutes. The deep orange mixture thus obtained was cooled to −30° C., and to the mixture was added one ml of a solution of the lactol 19 obtained above (50 mg, 0.148 mmole) in tetrahydrofuran. Then, the reaction mixture was treated following the procedure similar to that of Example 3, to yield the title compound 20 (34 mg, 55%) as a colorless oil.

NMR (CDCl$_3$); δ1.0–2.5 (m, 32H), 3.50 (m, 1H), 3.84 (m, 1H), 4.05 (m, 2H), 4.67 (m, 1H), 4.90–5.10 (m, 2H), 5.30–5.65 (m, 2H), 5.80 (m, 1H).

IR (CHCl$_3$); 3500, 2700–2400 (broad), 1705, 1640 cm$^{-1}$.

EXAMPLE 23

Preparation of (5Z,9S,11R)-9,11-dihydroxy-5,19-prostadienoic acid (compound 21)

The compound 20 obtained above (31 mg, 0.073 mmole) was dissolved in one ml of a mixture of acetic acid-water-tetrahydrofuran (65:35:10), and the solution was heated with stirring at 40°–45° C. for one hour and fifteen minutes. Then, the reaction mixture was treated following the procedure similar to that of Example 4, to yield the title compound 21 (22 mg, 89%) as a colorless oil.

NMR (CDCl$_3$); δ1.0–2.5 .m, 24H), 3.96 (m, 1H), 4.17 (m, 1H), 3.6–3.8 (broad, 3H), 4.90–5.10 (m, 2H), 5.30–5.60 (m, 2H), 5.80 (m, 1H).

IR (CHCl$_3$); 3450, 2700–2400 (broad), 1708, 1640 cm$^{-1}$.

The comprehensive scheme illustrating the reactions described in Examples 17–23 is shown below.

Reaction scheme for preparation of Δ¹⁹-PG
(Example 17-23)

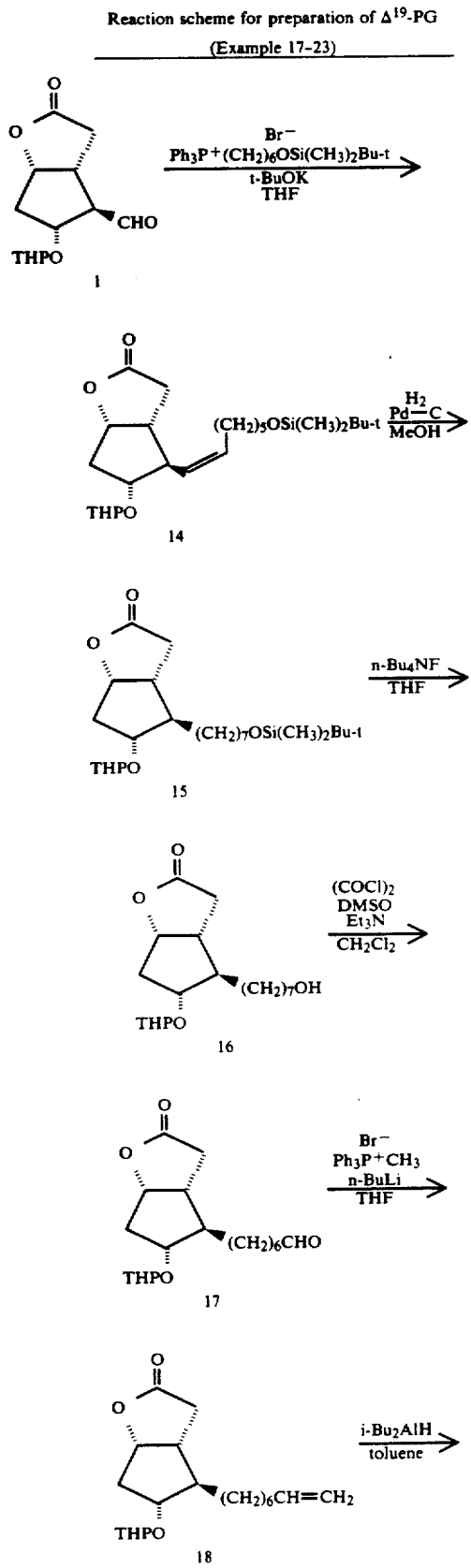

-continued
Reaction scheme for preparation of Δ¹⁹-PG
(Example 17-23)

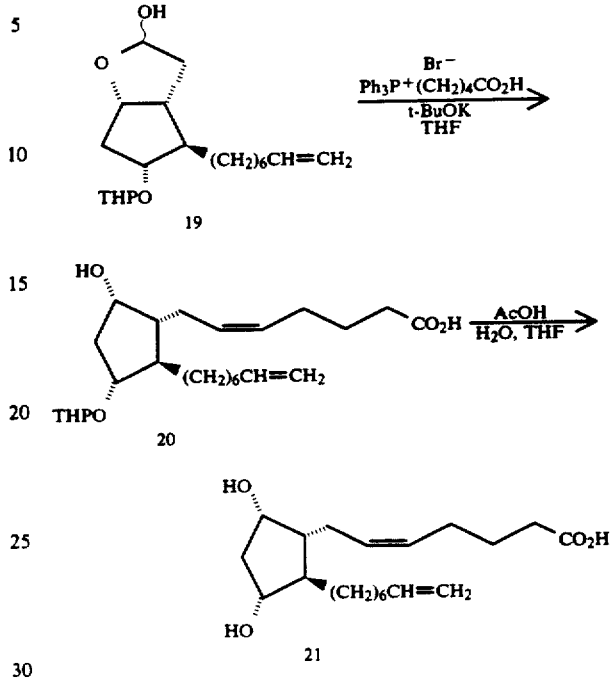

EXAMPLE 24

Preparation of
(1S,6R,7R)-2-oxa-3-oxo-6-[2-formyl-(1E)-ethenyl]-7-tetrahydropyranyloxy-cis-bicyclo[3.3.0]octane (compound 22)

The compound 1 obtained above (4.0 g, 15.73 mmole) and triphenylphosphoranylidene acetaldehyde (5.75 g, 18.88 mmole) were dissolved in benzene (50 ml), and the mixture was refluxed with stirring for one and half hours, and the solvent was evaporated off. The residue was purified with Lobar column (ethyl acetate:n-hexane=7:3), to yield the title compound 22 (3.29 g, 59%) as a pale yellow oil.

NMR (CDCl$_3$); δ1.40–1.80 (m, 6H), 2.25–3.00 (m, 6H), 3.35–3.60 (m, 1H), 3.70–3.95 (m, 1H), 4.00–4.30 (m, 1H), 4.66 (m, 1H), 5.02 (m, 1H), 6.18, 6.70 (each dd, J=8Hz, 16Hz, each 1H), 9.54 (d, J=8Hz, 1H).

EXAMPLE 25

Preparation of
(1S,6R,7R)-2-oxa-3-oxo-6-(2-formylethyl)-7-tetrahydropyranyloxy-cis-bicyclo[3.3.0]octane (compound 23)

The compound 22 obtained above (3.0 g, 10.70 mmole) was dissolved in ethyl acetate (60 ml), and 10% palladium-carbon (0.3 g) was added thereto, and the mixture was stirred under hydrogen at one atmospheric pressure for 30 minutes. The mixture was filtered and the filtrate was evaporated to yield the title compound 23 (3.0 g, 99%).

NMR (CDCl$_3$); δ1.40–1.80 (m, 6H), 2.20–2.90 (m, 10H), 3.40–3.60 (m, 1H), 3.70–4.10 (m, 2H), 4.64 (m, 1H), 4.98 (m, 1H), 9.80 (s, 1H).

EXAMPLE 26

Preparation of
(1S,6R,7R)-2-oxa-3-oxo-6-[(3Z)-octenyl]-7-tetrahydropyranyloxy-cis-bicyclo[3.3.0]octane (compound 24)

Pentyltriphenylphosphonium bromide (8.27 g, 20 mmole) was suspended in tetrahydrofuran (50 ml), and potassium tert-butoxide (2.69 g, 24 mmole) was added thereto under ice cooling, and the mixture was stirred at the same temperature for half an hour. The deep orange mixture thus obtained was cooled to −78° C., and 10 ml of a solution of the compound 23 obtained above (2.82 g, 10 mmole) in tetrahydrofuran was added thereto. Then, the reaction mixture was treated following the procedure similar to that of Example 1, to yield the title compound 24 (2.0 g, 60%) as a colorless oil.

NMR (CDCl$_3$); δ0.90 (t, J=7Hz, 3H), 1.20–2.90 (m, 22H), 3.52 (m, 1H), 3.75–4.12 (m, 2H), 4.66 (m, 1H), 5.02 (m, 1H), 5.35 (m, 2H).

EXAMPLE 27

Preparation of
(1S,6R,7R)-2-oxa-3-oxo-6-[(3E)-octenyl]-7-tetrahydropyranyloxy-cis-bicyclo[3.3.0]octane (compound 25)

The compound 24 obtained above (1.30 g, 3.86 mmole) was dissolved in benzene (20 ml), and 5-mercapto-1-methyltetrazole disulfide (0.44 g, 1.93 mmole) and α,α'-azobis-isobutyronitrile (63 mg, 0.386 mmol) were added thereto, and the mixture was refluxed with stirring for two hours. Then, the reaction mixture was treated following the procedure similar to that of Example 2, to yield the title compound 25 (1.05 g, 80%) as a colorless oil.

NMR (CDCl$_3$); δ0.89 (t, J=7Hz, 3H), 1.20–2.90 (m, 22H), 3.52 (m, 1H), 3.75–4.12 (m, 2H), 4.66 (m, 1H), 5.02 (m, 1H), 5.39 (m,2H).

EXAMPLE 28

Preparation of
(5Z,15E,9S,11R)-9-hydroxy-11-tetrahydropyranyloxy-5,15-prostadienoic acid (compound 27)

The compound 25 obtained above (336 mg, 1.0 mmole) was dissolved in toluene (12 ml), and 1M diisobutyl aluminum hydride in toluene (1.1 ml, 1.1 mmole) was added thereto at −78° C. Then, the mixture was treated following the prosedure similar to that of Example 3, to yield lactol 26 (285 mg, 84%).

IR (CHCl$_3$); 3600, 3400 cm$^{-1}$.

After 4-carboxybutyltriphenylphosphonium bromide (1.12 g, 2.53 mmole) was suspended in tetrahydrofuran (15 ml), potassium tert-butoxide (623 mg, 5.56 mmole) was added thereto under ice cooling, and the mixture was stirred at the same temperature for 30 minutes. The resultant red mixture was cooled to −30° C., and 6 ml of a solution of the lactol 26 obtained above (285 mg, 0.843 mmole) in tetrahydrofuran was added thereto. Then, the reaction mixture was treated following the procedure similar to that of Example 3, to yield 210 mg of the title compound as a colorless oil (yield 59%).

NMR (CDCl$_3$); δ0.88 (t, J=7Hz, 3H), 1.20–2.40 (m, 30H), 3.55 (m, 1H), 3.87 (m, 1H), 4.00–4.28 (m, 2H), 4.70 (m, 1H), 5.42 (m, 4H).

EXAMPLE 29

Preparation of
(5Z,15E,9S,11R)-9,11-dihydroxy-5,15-prostadienoic acid (compound 28)

The compound 27 obtained above (200 mg, 0.474 mmole) was dissolved in 3 ml of a mixture of acetic acid, water, and tetrahydrofuran (65:35:10). The mixture was heated at 40°–45° C. with stirring for one and half hours. Then, the reaction mixture was treated following the procedure similar to that of Example 4, to yield 128 mg of the title compound 28 as a colorless oil (yield 80%).

NMR (CDCl$_3$); δ0.89 (t, J=7Hz, 3H), 1.20–2.30 (m, 20H), 2.32 (t, J=6Hz, 2H), 3.95 (broad s, 1H), 4.14 (broad s, 1H), 4.4–6.1 (broad, 3H), 5.43 (m, 4H).

IR (CHCl$_3$); 3490, 2700–2400 (broad), 1708 cm$^{-1}$.

EXAMPLE 30

Prepraration of
(5Z,15E,9S,11R)-9,11-dihydroxy-5,15-prostadienoic acid isopropyl ester (compound 29)

The compound 28 obtained obove (237 mg, 0.70 mmole) was dissolved in acetonitrile (3 ml), and 1,8-diazabicyclo[5.4.0]-7-undecene (0.178 ml, 1.2 mmole) and isopropyl iodide (0.12 ml, 1.2 mmole) were added thereto and the mixture was stirred at room temperature for 15 hours. Then, the reaction mixture was treated following the procedure similar to that of Example 5, to yield 266 mg of the title compound 29 as a colorless oil (quantitative).

NMR (CDCl$_3$); δ0.89 (t, J=7Hz, 3H), 1.23 (d, J=6Hz, 6H), 1.20–2.25 (m, 22H), 2.30 (t, J=6Hz, 2H), 3.97 (broad s, 1H), 4.18 (broad s, 1H), 5.01 (sept, J=6Hz, 1H), 5.43 (m, 4H).

IR (CHCl$_3$); 3496, 1714 cm$^{-1}$.

EXAMPLE 31

Preparation of
(1S,6R,7R)-2-oxa-3-oxo-6-[(3Z)-decenyl]-7-tetrahydropyranyloxy-cis-bicyclo[3.3.0]octane (compound 24')

Heptyltriphenylphosphonium bromide (10.94 g, 24.8 mmole) was suspended in tetrahydrofuran (50 ml), and potassium tert-butoxide (3.33 g, 29.76 mmole) was added thereto under ice cooling, and the mixture was stirrd at the same temperature for 30 minutes. The deep orange mixture thus obtained was cooled to −78° C., and 10 ml of a solution of the compound 23 obtained above (3.5 g, 12.4 mmole) in tetrahydrofuran was added thereto. Then, the reaction mixture was treated following the procedure similar to that of Example 1, to yield the title compound 24' (2.09 g, 46%) as a colorless oil.

NMR (CDCl$_3$); δ0.89 (t, J=7Hz, 3H), 1.20–2.80 (m, 26H), 3.40–3.60 (m, 1H), 3.60–4.18 (m, 2H), 4.66 (m, 1H), 5.02 (m, 1H), 5.36 (m, 2H).

EXAMPLE 32

Preparation of
(1S,6R,7R)-2-oxa-3-oxo-6-[(3E)-decenyl]-7-tetrahydropyranyloxy-cis-bicyclo[3.3.0]octane (compound 25')

The compound 24' obtained above (1.0 g, 2.74 mmole) was dissolved in benzene (20 ml), and 5-mercapto-1-methyltetrazole disulfide (316 mg, 1.37 mmole) and α,α'-azobis-isobutyronitrile (45 mg, 0.274 mmol) were added thereto, and the mixture was refluxed with stirring for two hours. Then, the reaction mixture was treated following the procedure similar to that of Example 2, to yield the title compound 25' (320 mg, 32%) as a colorless oil.

NMR (CDCl$_3$); δ0.88 (t, J=7Hz, 3H), 1.20–2.85 (m, 26H), 3.40–3.55 (m, 1H), 3.75–3.96 (m, 1H), 4.16–4.20 (m, 1H), 4.66 (m, 1H), 5.02 (m, 1H), 5.40 (m, 2H).

EXAMPLE 33

Preparation of (5Z,15E,9S,11R)-20-ethyl-9-hydroxy-11-tetrahydropyranyloxy-5,15-prostadienoic acid (compound 27')

The compound 25, obtained above (550 mg, 1.51 mmole) was dissolved in toluene (20 ml), and 1M diisobutyl aluminum hydride in toluene (1.66 ml, 1.66 mmole) was added thereto at −78° C. Then, the mixture was treated following the procedure similar to that of Example 3, to yield lactol 26' (550 mg, 99%).

IR (CHCl$_3$); 3600, 3400 cm$^{-1}$.

After 4-carboxybutyltriphenylphosphonium bromide (1.33 g, 3.0 mmole) was suspended in tetrahydrofuran (15 ml), potassium tert-butoxide (672 mg, 6.0 mmole) was added thereto under ice cooling, and the mixture was stirred at the same temperature for 30 minutes. The resultant red mixture was cooled to −30, and 15 ml of a solution of the lactol 26' obtained above (550 mg, 1.50 mmole) in tetrahydrofuran was added thereto. Then, the reaction mixture was treated following the procedure similar to that of Example 3, to yield 484 mg of the title compound 27' as a colorless oil (yield 72%).

NMR (CDCl$_3$); δ0.89 (t, J=7Hz, 3H), 1.20–2.42 (m, 34H), 3.55 (m, 1H), 3.88 (m, 1H), 4.00–4.30 (m, 2H), 4.71 (m, 1H), 5.42 (m, 4H).

EXAMPLE 34

Preparation of (5Z,15E,9S,11R)-20-ethyl-9,11-dihydroxy-5,15-prostadienoic acid (compound 28')

The compound 27' obtained above (242 mg, 0.537 mmole) was dissolved in 3 ml of a mixture of acetic acid, water, and tetrahydrofuran (65:35:10). The mixture was heated at 40°–45° C. with stirring for one and half hours. Then, the reaction mixture was treated following the procedure similar to that of Example 4, to yield 87 mg of the title compound 28' as a colorless oil (yield 44%).

NMR (CDCl$_3$); δ0.88 (t, J=7Hz, 3H), 1.20–2.30 (m, 24H), 2.36 (t, J=7Hz, 2H), 3.98 (broad s, 1H), 4.17 (broad s, 1H), 4.1–5.3 (broad, 3H), 5.42 (m, 4H).

IR (CHCl$_3$); 3498, 2700–2400 (broad), 1708 cm$^{-1}$.

EXAMPLE 35

Preparation of (5Z,15E,9S,11R)-20-ethyl-9,11-dihydroxy-5,15-prostadienoic acid isopropyl ester (compound 29')

The compound 28' obtained obove (87 mg, 0.237 mmole) was dissolved in acetonitrile (2 ml), and 1,8-diazabicyclo[5.4.0]-7-undecene (0.716 ml, 4.8 mmole) and isopropyl iodide (0.24 ml, 2.4 mmole) were added thereto and the mixture was stirred at room temperature for 16 hours. Then, the reaction mixture was treated following the procedure similar to that of Example 5, to yield 62 mg of the title compound 29' as a colorless oil (yield 64%).

NMR (CDCl$_3$); δ0.88 (t, J=7Hz, 3H), 1.22 (d, J=6Hz, 6H), 1.20–2.30 (m, 26H), 2.29 (t, J=7Hz, 2H), 3.96 (broad s, 1H), 4.17 (broad s, 1H), 5.01 (sept, J=6Hz, 1H), 5.43 (m, 4H).

IR (CHCl$_3$); 3504, 1714 cm$^{-1}$.

The comprehensive scheme illustrating the reactions described in Examples 24–35 is shown below.

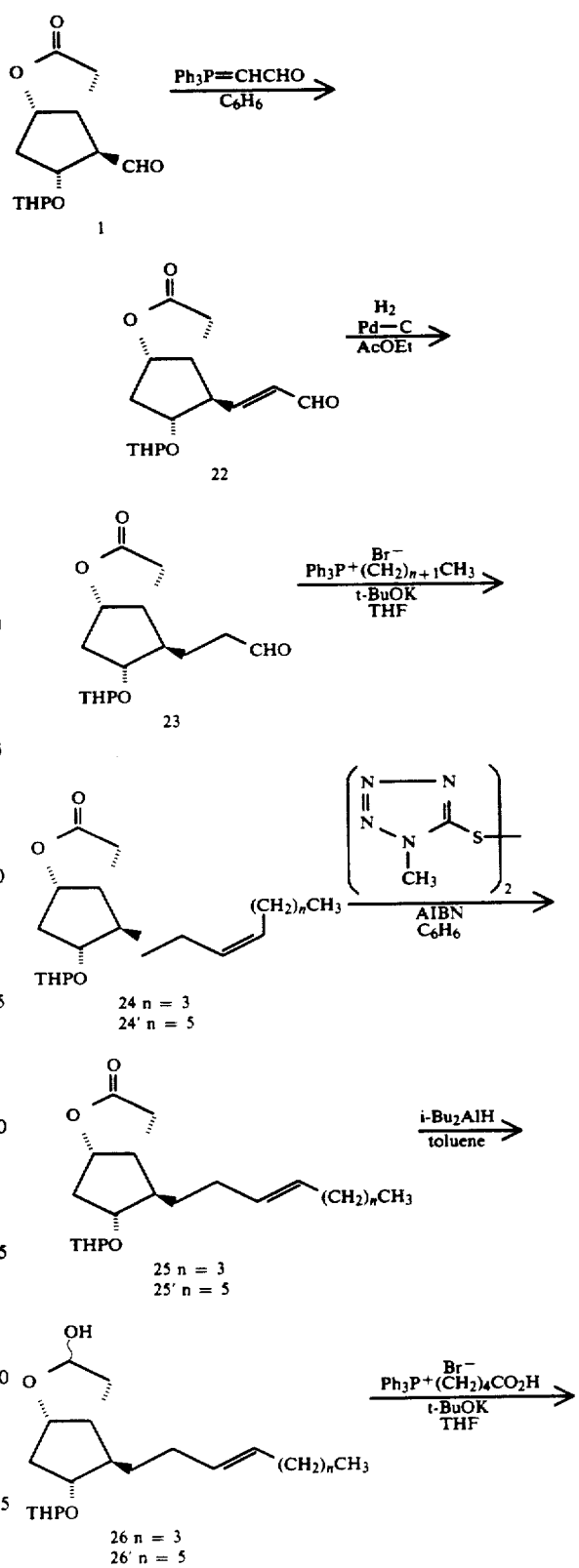

Reaction scheme for preparation of $\Delta^{15}$-PG

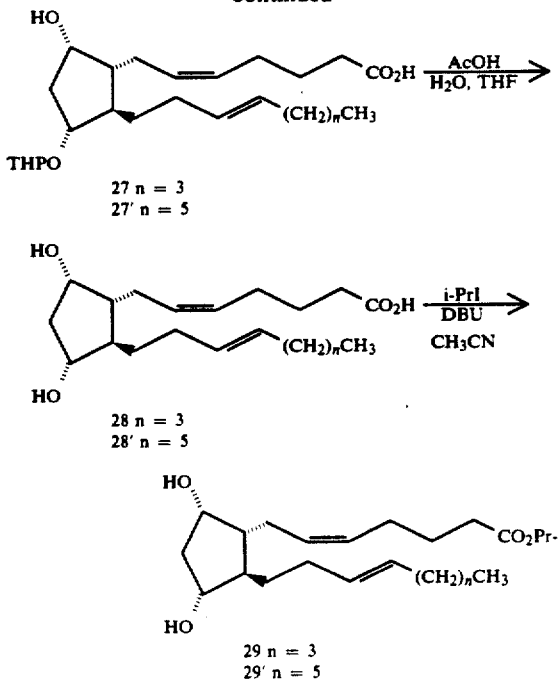

27 n = 3
27' n = 5

28 n = 3
28' n = 5

29 n = 3
29' n = 5

EXAMPLE 36

Preparation of a sodium salt of (5Z,13E,9S,11R)-9,11-dihydroxy-5,13-prostadienoic acid The compound 6, (5Z,13E,9S,11R)-9,11-dihydroxy-5,13-prostadienoic acid obtained above (169 mg, 0.5 mmole) was dissolved in 1N aqueous sodium hydroxide solution (0.475 ml, 0.475 mmole), and the solution was diluted with distilled water (4 ml), and then the diluted solution was filtered. The filtrate was lyophilized over eight hours to yield a colorless crystal (194 mg). The material was triturated with diisopropyl ether and filtered. The resultant filter cake was washed with diisopropyl ether to yield 153 mg of the title compound (yield 85%) as a colorless crystal.

M.p.; 40°–43° C.
NMR (CD$_3$OD); δ0.89 (t, J=7Hz, 3H), 1.2–2.4 (m, 22H), 3.77 (m, 1H), 4.07 (m, 1H), 5.19–5.60 (m, 4H).
IR (Nujol); 3350, 1565, 1550, 1425 cm$^{-1}$.
Elemental analysis (for C$_{20}$H$_{33}$O$_4$Na·1.5H$_2$O)
Theory: C,61.83; H,9.34; Na,5.90%.
Found: C,62.14; H,9.44; Na,5.94%.

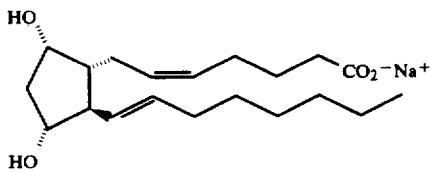

EXAMPLE 37

Preparation of (5Z,13E,9S,11R)-9,11-dihydroxy-5,13-prostadienoic acid p-methoxybenzyl ammonium After (5Z,13E,9S,11R)-9,11-dihydroxy-5,13-prostadienoic acid (compound 6) (208 mg, 0.615 mmole) was dissolved in dried diethyl ether (3 ml), p-methoxybenzylamine (85 μl, 0.645 mmole) was added thereto. The resultant crystal was taken by filtration, and washed with diethyl ether to yield a colorless crystal (278 mg). The product was recrystallized from dichloromethane-diethyl ether to yield 245 mg of the title compound (yield 84%) as a colorless crystal.

M.p.: 101°–104° C.
NMR (D$_2$O); δ0.85 (t, J=7Hz, 3H), 1.1–2.4 (m, 22H), 3.79 (s, 3H), 3.82 (m, 1H), 4.05 (m, 1H), 4.09 (s, 2H), 5.15–5.60 (m, 4H), 7.00, 7.40 (each d, J=8Hz, each 2H).
IR (Nujol); 3375, 1610, 1560, 1515, 1410 cm$^{-1}$.
Elemental analysis (for C$_{28}$H$_{45}$O$_5$N)
Theory; C,70.70; H,9.54; N,2.95%.
Found: C,70.31; H,9.40; N,2.93%.

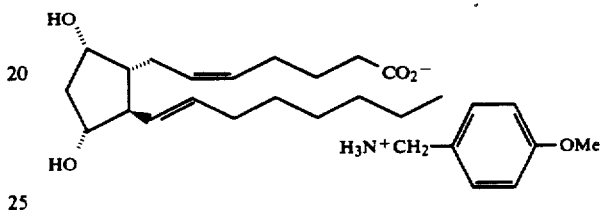

EXAMPLE 38

Preparation of (1S,6R,7R)-2-oxa-3-oxo-6-(2-methoxyvinyl)-7-tetrahydropyranyloxy-cis-bicyclo[3.3.0]octane (compound 103)

Methoxymethyltriphenylphosphonium chloride (13.2 g, 38.4 mmole) was suspended in tetrahydrofuran (132 ml), and potassium tert-butoxide (4.32 g, 38.4 mmole) was added thereto under ice cooling, and the mixture was stirrd at the same temperature for 10 minutes. The red mixture thus obtained was cooled to −35° C., and 50 ml of a solution of the compound 1 obtained above (4.9 g, 19.2 mmole) in tetrahydrofuran was added thereto. The reaction mixture was allowed to warm to room temparature over one hour, and an aqueous solution of ammonium chloride was added thereto, and the mixture was evaporated in vacuo to remove most of the tetrahydrofuran. The residue was extracted with ether, and the extract was washed with diluted hydrochloric acid, aqueous sodium bicarbonate and brine, successively. Then, the extract was dried over anhydrous magnesium sulfate, and the solvent was evaporated off. The resultant brown solid material (13.6 g) was chromatographed over silica gel (139 g), eluting with 1:1 of ethyl acetate:n-hexane, to yield 6.7 g of an yellow oil. The product was purified with Lobar column (ethyl acetate:n-hexane=2:1) to yield 3.47 g of the title compound 103 as a colorless oil (yield 64%) which is a mixture of geometrical isomers in terms of the vinyl group.

NMR (CDCl$_3$); δ1.40–2.85 (m, 12H), 3.45 (m, 1H), 3.52, 3.53, 3.60, 3.61 (each s, 3H total), 3.75–4.17 (m, 2H), 4.45–4.60 (m, 1H), 4.65–4.75 (m, 1H), 4.85–5.05 (m, 1H), 5.89–5.98, 6.33–6.45 (each m,1H total).
IR (CHCl$_3$); 1763, 1654, 1112, 1033 cm$^{-1}$.

EXAMPLE 39

Preparation of (1S,6R,7R)-2-oxa-3-oxo-6-formylmethyl-7-tetrahydropyranyloxy-cis-bicyclo[3.3.0]octane (compound 104)

The compound 103 obtained above (3.94 g, 13.97 mmole) was dissolved in tetrahydrofuran-water (10:1, 66 ml), and to the solution was added mercuric acetate (5.34 g, 16.77 mmole), and the mixture was stirred at room temperature for 30 minutes. Then, potassium iodide (11.6 g, 69.85 mmol)-water (20 ml) was added thereto. The mixture was stirred for 30 minutes, and concentrated in vacuo. The residue was extracted with chloroform. The extract was washed with aqueous potassium iodide and water, and dried over anhydrous sodium sulfate, and then the solvent was evaporated off, to yield 3.52 g of the title compound 104 (yield 94%).

NMR (CDCl$_3$); $\delta$1.40-1.92 (m, 8H), 2.08-2.96 (m, 6H), 3.40-4.10 (m, 3H), 4.62-4.74 (m, 1H), 4.94-5.02 (m, 1H), 9.88 (t, J=1Hz, 1H).

EXAMPLE 40

Preparation of
(1S,6R,7R)-2-oxa-3-oxo-6-[(2Z)-octenyl]-7-tetrahydropyranyloxy-cis-bicyclo[3.3.0]octane (compound 105)

After n-hexyltriphenylphosphonium bromide (11.47 g, 26.84 mmole) was suspended in tetrahydrofuran (110 ml) and potassium tert-butoxide (3.01 g, 26.84 mmole) was added thereto under ice cooling, the mixture was stirrd at room temperature for 30 minutes. The mixture was cooled to 0° C., and 36 ml of a solution of the compound 104 obtained above (3.60 g, 13.42 mmole) in tetrahydrofuran was added thereto, and the mixture was stirred for 30 minutes. An aqueous solution of ammonium chloride was added thereto, and the mixture was concentrated in vacuo. The residue was extracted with ethyl acetate, and the extract was washed with brine. Then, the washed extract was dried over anhydrous magnesium sulfate, and the solvent was evaporated off. The resultant residue was chromatographed over silica gel (20 g), eluting with 600 ml of 1:4 ethyl acetate:n-hexane, to yield 4.24 g of the title compound 105 (yield 94%).

NMR (CDCl$_3$); $\delta$0.89 (t, J=7Hz, 3H), 1.18-1.84 (m, 14H), 1.88-2.32 (m, 6H), 2.48-2.86 (m, 2H), 3.44-4.12 (m, 3H), 4.62-4.68 (m, 1H), 4.94-5.08 (m, 1H), 5.24-5.56 (m, 2H).

EXAMPLE 41

Preparation of
(1S,6R,7R)-2-oxa-3-oxo-6-[(2E)-octenyl]-7-tetrahydropyranyloxy-cis-bicyclo[3.3.0]octane (compound 107)

The compound 105 obtained above (4.20 g, 12.48 mmole) was dissolved in benzene (125 ml), and 5-mercapto-1-methyltetrazole disulfide (1.44 g, 6.42 mmole) and $\alpha,\alpha'$-azobis-isobutyronitrile (0.205 g, 1.25 mmole) were added thereto, and the mixture was refluxed for 3 hours. The mixture was allowed to cool to room temperature, and washed with aqueous sodium carbonate and water, and then dried over anhydrous sodium sulfate. The solvent was evaporated off in vacuo. The resultant residue was chromatographed over silica gel (100 g) eluting with 100 ml of 1:4 ethyl acetate:n-hexane, to yield the title compound 107 (3.624 g, 86%).

NMR (CDCl$_3$); $\delta$0.89 (t, J=7Hz, 3H), 1.18-2.28 (m, 20H), 2.46-2.86 (m, 2H), 3.42-4.12 (m, 3H), 4.62-4.68 (m, 1H), 4.92-5.06 (m, 1H), 5.24-5.56 (m, 2H).

EXAMPLE 42

Preparation of
(5Z,14E,9S,11R)-9-hydroxy-11-tetrahydropyranyloxy-5,14-prostadienoic acid (compound 109)

The compound 107 obtained above (3.60 g, 10.7 mmole) was dissolved in tetrahydrofuran (72 ml), and 1M diisobutyl aluminum hydride in toluene (10.7 ml) was added thereto at −78° C. The reaction was stirred at the same temperature for one hour, and then ethyl acetate (2 ml) was added thereto, and the temperature was allowed to warm to 0° C. At the same temperature, aqueous ammonium chloride (5 ml), aqueous potassium sodium tartrate (40 ml) and ethyl acetate (80 ml) were added thereto successively. The mixture was stirred for one hour, and the organic layer was isolated. The layer was dried over anhydrous sodium sulfate, and then the solvent was evaporated off, to yield lactol 108 (3.39 g, 93%).

NMR (CDCl$_3$); $\delta$0.89 (t, J=7Hz, 1H), 1.18-1.40 (m, 8H), 1.42-1.84 (m, 6H), 1.84-2.08 (m, 6H), 2.16-2.52 (m, 2H), 3.40-4.14 (m, 3H), 4.56-4.78 (m, 2H), 5.02-5.64 (m, 3H).

After (4-carboxybutyl)triphenylphosphonium bromide (8.86 g, 20 mmole) was suspended in tetrahydrofuran (100 ml), a potassium tert-butoxide (4.48 g, 40 mmole) was added thereto under ice cooling, and the mixture was stirred at room temperature for one hour. The resultant mixture was cooled to −78° C., and 50 ml of a solution of the lactol 108 obtained above (3.39 mg, 10 mmole) in tetrahydrofuran was added thereto. The mixture was allowed to warm to room temperature over one hour. To the mixture was added a solution of ammonium chloride in water under ice cooling, and then the mixture was concentrated in vacuo to remove most of the tetrahydrofuran. To the residue, cooled and diluted hydrochloric acid was added, and the mixture was extracted with ethyl acetate. The extract was dried over anhydrous sodium sulfate, and the solvent was evaporated off. To the residue was added ether, and an insoluble material was filtered off. The filtrate was concentrated, and the residue was purified with Lobar column (ethyl acetate:n-hexane:acetic acid=50:50:1), to yield the title compound 109 (3.42 g, 77%).

NMR (CDCl$_3$); 0.89 (t, J=7Hz, 3H), 1.18-2.30 (m, 26H), 2.34 (t, J=7Hz, 2H), 3.42-3.56 (m, 1H), 3.78-3.96 (m, 1H), 3.98-4.18 (m, 2H), 4.58-4.76 (m, 1H), 5.38-5.58 (m, 4H).

EXAMPLE 43

Preparation of
(5Z,14E,9S,11R)-9,11-dihydroxy-5,14-prostadienoic acid methyl ester (compound 111)

The compound 109 obtained above (3.42 g, 7.73 mmole) was dissolved in a mixture of acetic acid (27 ml), tetrahydrofuran (9 ml) and water (9 ml). The solution was stirred at 65° C. for three hours, and then the solvent was evaporated off. The residue was dissolved in ethyl acetate, and the solution was washed with brine, dried over anhydrous sodium sulfate, and evaporated. The residue was chromatographed over Lobar column (ethyl acetate:n-hexane:acetic acid=50:50:1), to yield 2.31 g of the crude dihydroxycarboxylate (compound 110) (yield 88%). The compound 110 (1.85 g, 5.46 mmole) was dissolved in acetonitrile (18 ml), and 1,8-diazabicyclo[5.4.0]-7-undecene (2.50 g, 16.40 mmole) and then methyl iodide (3.88 g, 27.33 mmole)

were added thereto, and the mixture was stirred at room temperature for three hours. The mixture was concentrated in vacuo, and the residue was dissolved in ethyl acetate, and the solution was washed successively with diluted hydrochloric acid and brine, and dried over anhydrous magnesium sulfate. The solvent was evaporated off, and the residue was purified with Lobar colum (methylene chloride:methanol=97:3), to yield the title compound 111 (1.59 g, 83%).

NMR (CDCl$_3$); δ0.89 (t, J=7Hz, 3H), 1.18-1.55 (m, 6H), 1.60-2.30 (m, 15H), 2.34 (t, J=7Hz, 2H), 3.67 (s, 3H), 3.94-4.02 (m, 1H), 4.16-4.22 (m, 1H), 5.30-5.58 (m, 4H).

EXAMPLE 44

Preparation of (5Z,14E,9S,11R)-9,11-dihydroxy-5,14-prostadienoic acid (compound 110)

The compound 111 obtained obove (720 mg, 2.04 mmole) was dissolved in methanol (4 ml), and 1 N sodium hydroxide solution was added thereto, and the mixture was stirred at room temperature for two hours. The methanol was evaporated off in vacuo, and then the residue was acidified by adding diluted hydrochloric acid under ice cooling. The acidified mixture was extracted with ethyl acetate. The extract was washed with brine, and dried over anhydrous sodium sulfate, and the solvent was evaporated off. The residue was chromatographed over silicic acid (7 g), eluting with 100 ml of 1:1 of ethyl acetate:n-hexane, to yield the title compound 110 (681 mg, 99%).

NMR (CDCl$_3$); δ0.89 (t, J=7Hz, 3H), 1.18-1.56 (m, 6H), 1.60-2.30 (m, 14H), 2.36 (t, J=7Hz, 2H), 3.92-4.02 (m, 1H), 4.16-4.20 (m, 1H), 4.60 (broad, 3H), 5.30-5.58 (m, 4H).

IR (CHCl$_3$); 3396, 2660(broad), 1707 cm$^{-1}$.

The comprehensive scheme illustrating the reactions described in Examples 38-44 is shown below.

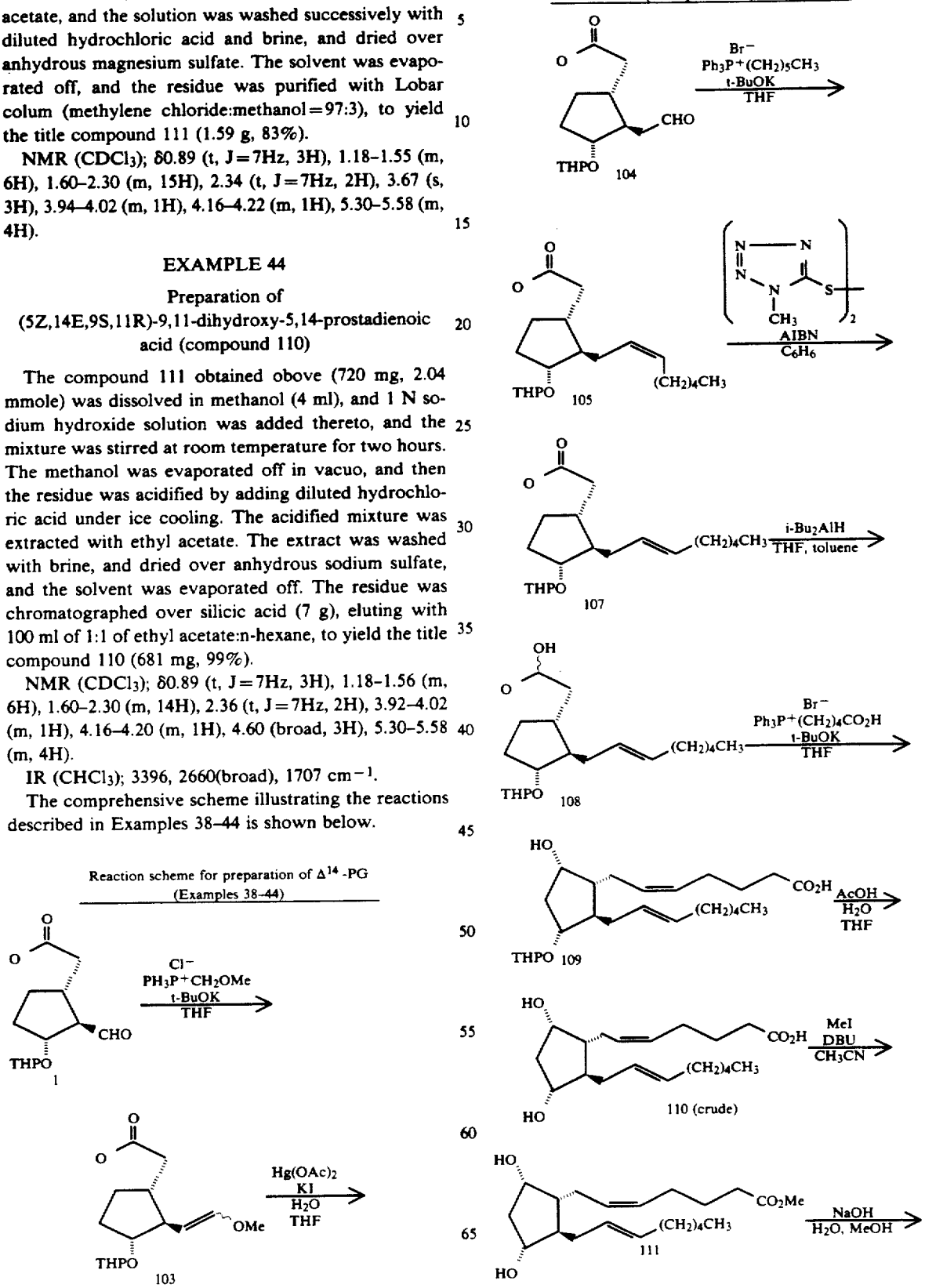

-continued
Reaction scheme for preparation of Δ14 -PG
(Examples 38-44)

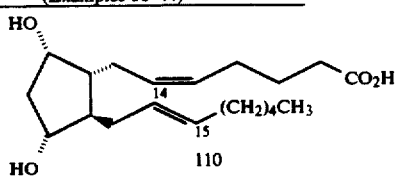

EXAMPLE 45

Preparation of (5Z,13Z,9S,11R)-9-hydroxy-11-tetrahydropyranyloxy-5,13-prostadienoic acid methyl ester (compound 114)

The compound 2 obtained above (12.66 g, 37.6 mmole) was dissolved in toluene (240 ml), and the solution was cooled to −78° C., and 60 ml of 0.94M solution of diisobutyl aluminum hydride in hexane was added thereto. Then, the mixture was treated following the procedure similar to that of Example 5 to yield lactol 112. After (4-carboxybutyl)triphenylphosphonium bromide (50.0 g, 112.8 mmole) was suspended in tetrahydrofuran (270 ml), potassium tert-butoxide (23.6 g, 210.6 mmole) was added thereto under ice cooling, and the mixture was stirred for 40 minutes. The resultant mixture was cooled to −15° C., and 100 ml of a solution of the lactol 12 obtained above in tetrahydrofuran was added thereto. Then, the reaction mixture was treated following the procedure similar to that of Example 42, to yield carboxy compound 113. The compound was dissolved in 240 ml of tetrahydrofuran-methanol mixture (5:1), and a slight exess amount of diazomethane-ether solution was added thereto. The solution was evaporated and the residue was chromatographed over silica gel (750 g) eluting with ethyl acetate-n-hexane (1:4), to yield 14.78 g of the title compound 114 (yield 90%).

NMR (CDCl$_3$); δ0.89 (t, J=7.5Hz, 3H), 1.19-2.38 (m, 25H), 2.33 (t, J=7.5Hz, 2H), 2.68-2.93 (m, 1H), 3.39-4.18 (m, 4H), 3.67 (s, 3H), 4.63-4.72 (m, 1H), 5.11-5.58 (m, 4H).

IR (CHCl$_3$); 3600, 3500, 1726 cm$^{-1}$.

EXAMPLE 46

Preparation of (5Z,13Z,9S,11R)-9,11-dihydroxy-5,13-prostadienoic acid methyl ester (compound 115)

The compound 114 (14.78 g, 33.9 mmole) was dissolved in a mixture of acetic acid (90 ml), tetrahydrofuran (30 ml) and water (30 ml), and the solution was stirred at 55° C. for five hours. After diluted with water, the solution was extracted with ethyl acetate, and the extract was washed with aqueous sodium bicarbonate and brine. The extract was dried over anhydrous sodium sulfate and evaporated. Then, the residue was chromatographed over silica gel (300 g) eluting with ethyl acetate-n-hexane (1:2), to yield 10.35 g of the title compound 115 (yield 87%).

NMR (CDCl$_3$); δ0.89 (t, J=7.5Hz, 3H), 1.20-2.40 (m, 19H), 2.36 (t, J=7.5Hz, 2H), 2.63-2.77 (m, 1H), 3.68 (s, H), 3.85-3.95 (m, 1H), 4.16-4.24 (m, 1H), 5.09-5.62 (m, 4H).

IR (CHCl$_3$); 3600, 3500, 1726 cm$^{-1}$.

EXAMPLE 47

Preparation of (5Z,13Z,9S,11R)-9,11-bis(tert-butyldimethylsilyloxy)-5,13-prostadienoic acid methyl ester (compound 116)

The compound 115 (10.35 g, 29.4 mmole) was dissolved in dimethylformamide (64 ml), and imidazole (9.01 g, 132 mmole) and tert-butyl dimethylsilyl chloride (17.73 g, 118 mmole) were added to the solution under ice cooling, and the mixture was stirred at room temperature for five hours. After diluted with ethyl acetate, the mixture was washed with brine, and dried over anhydrous sodium sulfate, and evaporated. Then, the residue was chromatographed over silica gel (750 g) eluting with ethyl acetate-n-hexane (1:50), to yield 16.34 g of the title compound 116 (yield 96%).

NMR (CDCl$_3$); δ−0.04, −0.02, 0.02, 0.05 (each s, each 3H), 0.85, 0.90 (each s, each 9H), 0.88 (t, J=7.5Hz, 3H), 1.18-2.26 (m, 19H), 2.29 (t, J=7.5Hz, 2H), 2.66-2.83 (m, 1H), 3.66 (s, 3H), 3.68-3.81 (m, 1H), 4.04-4.13 (m, 1H), 4.99-5.57 (m, 4H).

IR (CHCl$_3$); 1727 cm$^{-1}$.

EXAMPLE 48

Preparation of (5E,13E,9S,11R)-9,11-bis(tert-butyldimethylsilyloxy)-5,13-prostadienoic acid methyl ester (compound 117)

The compound 116 obtained above (7.27 g, 12.5 mmole) was dissolved in benzene (40 ml), and 5-mercapto-1-methyltetrazole disulfide (2.88 g, 12.5 mmole) and α,α'-azobis-isobutyronitrile (205 mg, 1.25 mmole) were added thereto, and the mixture was refluxed with stirring for 19 hours. Then, the reaction mixture was treated following the procedure similar to that of Example 41, to yield a residue. The residue was chromatographed over silica gel (330 g), eluting with ethyl acetate:n-hexane (1:50), to yield 5.34 g of a mixture of geometrical isomers with respect to the double bond. The material was further chromatographed over 10% silver nitrate-silica gel (500 g), eluting with ether-n-hexane (1:50), to yield 3.64 g of the title compound 117 (yield 50%).

NMR (CDCl$_3$); δ−0.02, −0.01, 0.01, 0.04 (each s, each 3H), 0.85, 0.89 (each s, each 9H), 0.89 (t, J=7.5Hz, 3H), 1.18-2.26 (m, 20H), 2.29 (t, J=7.5Hz, 2H), 3.66 (s, 3H), 3.70-3.83 (m, 1H), 4.02-4.11 (m, 1H), 5.03-5.53 (m, 4H).

IR (CHCl$_3$); 1727 cm$^{-1}$.

EXAMPLE 49

Preparation of (5E,13E,9S,11R)-9,11-dihydroxy-5,13prostadienoic acid methyl ester (compound 118)

The compound 117 obtained above (4.81 g, 8.28 mmole) was dissolved in 1.0M solution (41.4 ml) of tetra(n-butyl)ammonium fluoride in tetrahydrofuran solution (41.4 ml), and the solution was stirred at room temperature for 14 hours. After diluted with water, the mixture was extracted with ethyl acetate and washed with brine. The extract was dried over anhydrous sodium sulfate, and evaporated. Then, the residue was chromatographed over silica gel (330 g), eluting with ethyl acetate-n-hexane (1:1), to yield 2.81 g of the title compound 118 (yield 96%).

NMR (CDCl$_3$); 0.89 (t, J=7.5Hz, 3H), 1.20-2.32 (m, 20H), 2.31 (t, J=7.5Hz, 2H), 3.68 (s, 3H), 3.85-3.98 (m, 1H), 4.16-4.25 (m, 1H), 5.13-5.60 (m, 4H).

IR (CHCl₃); 3580, 3500, 1727 cm⁻¹.

EXAMPLE 50

Preparation of (5E,13E,9S,11R)-9,11-dihydroxy-5,13-prostadienoic acid (compound 119)

The compound 118 obtained above (2.81 g, 7.97 mmole) was dissolved in methanol (28 ml), and 1.0M aqueous potassium hydroxide (28 ml), and the mixture was stirred at 65° C. for two hours. The methanol was removed from the mixture in vacuo, and the residue was diluted with water. The aqueous solution was washed with ether. The aqueous phase was acidified with sodium bisulfate, and then the solution was extracted with ethyl acetate, and the extract was washed with brine. The washed extract was dried over anhydrous sodium sulfate, and evaporated. Then, the residue was chromatographed over silicic acid (13.5 g), eluting with ethyl acetate-n-hexane (1:2), to yield 2.70 g of the title compound 119 (almost quantitative).

NMR (CDCl₃); δ0.88 (t, J=7.5Hz, 3H), 1.17–2.40 (m, 20H), 2.34 (t, J=7.5Hz, 2H), 3.80–4.06 (m, 1H), 4.06–4.33 (m, 1H), 5.13–5.60 (m, 4H).

IR (CHCl₃); 3400, 2660 (broad), 1705 cm⁻¹.

The comprehensive scheme illustrating the reactions described in Examples 45–50 is shown below.

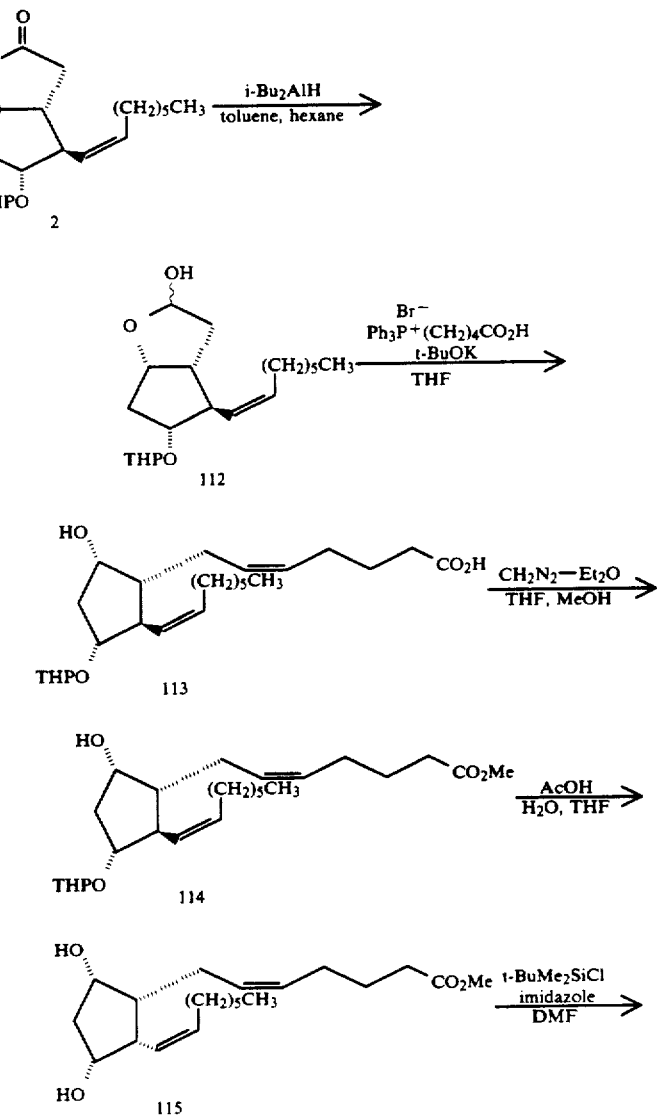

-continued
Reaction scheme of preparation of Δ⁵trans (E)-PG
(Examples 45-50)

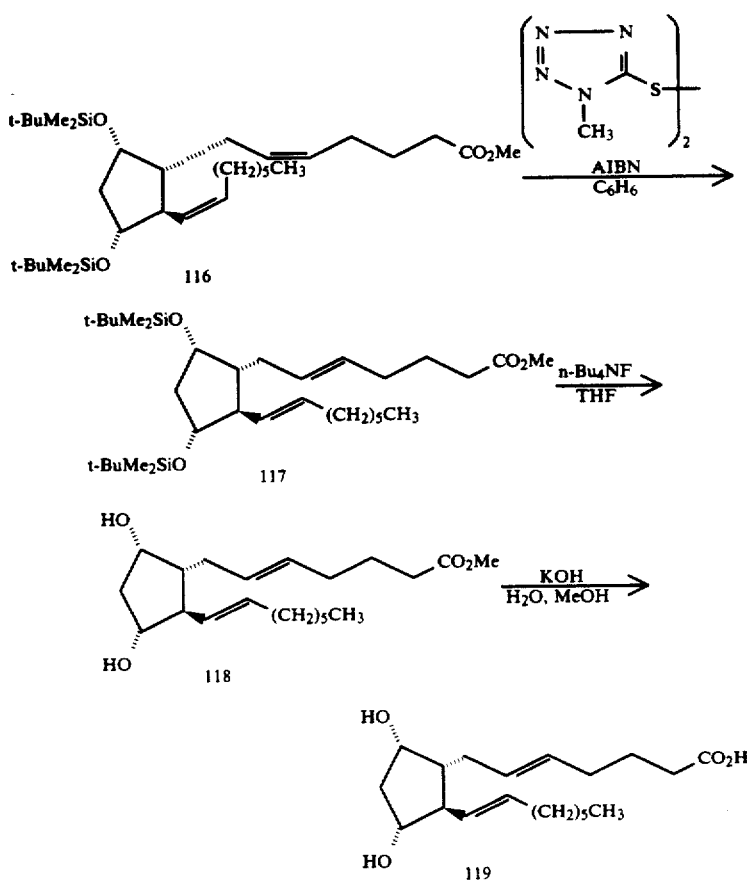

EXAMPLE 51

Preparation of (5Z,13E,15E,9S,11R)-9,11-diacetoxy-5,13,15-prostatrienoic acid (compound 121)

After a mixture comprising prostaglandin $F_{2\alpha}$ (3.545 g, 10 mmole), pyridine (10 ml), and acetic anhydride (10 ml) was stirred at room temperature for two hours, the solvent was evaporated off in vacuo. The residue was dissolved in ethyl acetate, and the solution was washed with diluted hydrochloric acid and brine. The washed solution was dried over anhydrous sodium sulfate, and evaporated. Then, the residue was chromatographed over silica gel (30 g), eluting with ethyl acetate-n-hexane (1:1, 300 ml), to yield 4.50 g of prostaglandin $F_{2\alpha}$ 9,11,15-O-triacetate 120 (yield 94%).

NMR (CDCl₃); δ0.88 (t, J=7Hz, 3H), 1.20–1.42 (m, 6H), 1.48–1.78 (m, 6H), 2.02, 2.06, 2.07 (each s, each 3H), 1.90–2.22 (m, 4H), 2.34 (t, J=7Hz, 2H), 2.42–2.62 (m, 2H), 4.82–4.92 (m, 1H), 5.06–5.14 (m, 1H), 5.20–5.30 (m, 1H), 5.35–5.40 (m, 2H), 5.50–5.60 (m, 2H).

The compound 120 obtained above (4.50 g, 9.36 mmole) was dissolved in tetrahydrofuran (45 ml), and tetrakis(triphenylphosphine)palladium (1.082 g, 0.936 mmole) and triethylamine (1.89 g, 18.72 mmole) were added thereto, and the mixture was stirred at 65° C. in an atmosphere of nitrogen for two hours. The solvent was evaporated off, and the residue was chromatographed over silica gel (40 g), eluting with ethyl acetate-n-hexane (1:1, 200 ml), to yield 3.90 g of the title compound 121 (yield 99%).

NMR (CDCl₃); δ0.88 (t, J=7Hz, 3H), 1.18–1.42 (m, 4H), 1.48–1.76 (m, 4H), 2.02, 2.07 (each s, each 3H), 1.96–2.22 (m, 6H), 2.34 (t, J=7Hz, 2H), 2.45–2.65 (m, 2H), 4.82–4.94 (m, 1H), 5.04–5.15 (m, 1H), 5.30–5.50 (m, 3H), 5.58–5.72 (m, 1H), 5.82–6.18 (m, 2H).

EXAMPLE 52

Preparation of (5Z,13E,15E,9S,11R)-9,11-dihydroxy-5,13,15-prostatrienoic acid (compound 122)

The compound 121 obtained above (3.90 g, 9.27 mmole) was dissolved in methanol (40 ml), and 10% aqueous sodium hydroxide was added to the solution, and the mixture was stirred at room temperature for one hour. Then, the mixture was treated following the procedure similar to that of Example 44 to yield a residue (2.84 g). The residue was purified with Lobar column (ethyl acetate:n-hexane:acetic acid=50:50:1), to yield the title compound 122 (2.67 g, 84%).

NMR (CDCl₃); δ0.89 (t, J=7Hz, 3H), 1.22–1.40 (m, 4H), 1.42–1.82 (m, 4H), 2.00–2.30 (m, 8H), 2.36 (t, J=7Hz), 2H), 3.92–4.02 (m, 1H), 4.16–4.22 (m, 1H), 5.20 (broad, 3H), 5.30–5.50 (m, 3H), 5.56–5.70 (m, 1H), 5.94–6.18 (m, 2H).

IR (Neat); 3376, 2620 (broad), 1706 cm⁻¹.

The comprehensive scheme illustrating the reactions described in Examples 51–52 is shown below.

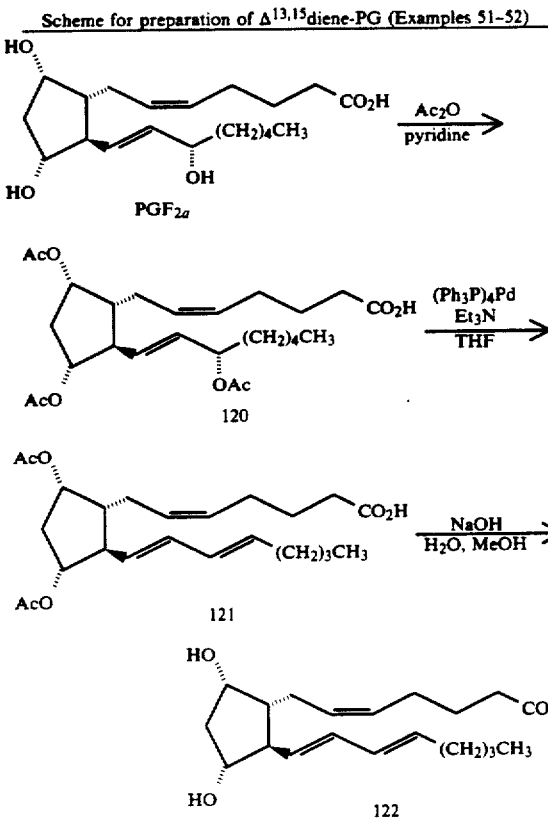

Scheme for preparation of Δ[13,15]diene-PG (Examples 51–52)

EXAMPLE 53

Preparation of (5Z,13E,9S,11R)-9,11-dihydroxy-5,13-prostadienoic acid diphenylmethyl ester (compound 123)

The compound 6 obtained above (820 mg, 2.42 mmole) and diphenyldiazomethane (565 mg, 2.88 mmole) were dissolved in methylene chloride (14 ml), and the solution was refluxed for two hours. The reaction was concentrated in vacuo, and the residue was chromatographed over silica gel (14 g), eluting with ethyl acetate-n-hexane (1:10–2:1), to yield the title compound 123 (1.16 g, 95%) as a colorless oil.

NMR (CDCl$_3$); δ0.88 (t, J=7Hz, 3H), 1.20–2.30 (m, 22H), 2.44 (t, J=7Hz, 2H), 3.91 (m, 1H), 4.13 (m, 1H), 5.15–5.60 (m, 4H), 6.89 (s, 1H), 7.32 (m, 10H).

IR (CHCl$_3$); 3590, 3510, 1726, 1599 cm$^{-1}$.

EXAMPLE 54

Preparation of (5Z,13E,9S)-9-hydroxy-11-oxo-5,13-prostadienoic acid diphenylmethyl ester (compound 124) and (5Z,13E,11R)-9-oxo-11-hydroxy-5,13-prostadienoic acid diphenylmethyl ester (compound 125)

The compound 123 obtained above (1.13 g, 2.24 mmole) was dissolved in acetone (20 ml), and the solution was cooled to −20° C., and Jones reagent (1.3 ml) was added dropwise thereto. After stirred at the same temperature for one hour, isopropanol (0.5 ml) was added to the mixture, and the mixture was allowed to warm to 0° C. The warmed mixture was diluted with ethyl acetate-n-hexane (1:2, 80 ml), the supernatant was passed through silica gel (10 g). The solution was evaporated to yield an yellow oil (0.97 g), and the oil was purified with Lobar column (ethyl acetate-n-hexane=1:3). There were obtained the oily title compound 124 (405 mg, 36%), a mixture (105 mg, 9%) of the compound 124 and the title compound 125, and the compound 125 as a crystal (240 mg, 21%) in the order of elution.

124: NMR (CDCl$_3$); δ0.87 (t, J=7Hz, 3H), 1.15–2.50 (m, 22H), 2.75 (dd, J=12.5, 7.5Hz, 1H), 4.47 (m, W½=7Hz, 1H), 5.19 (dd, J=15, 7.5Hz, 1H), 5.42 (m, 2H), 5.56 (dt, J=15, 6Hz, 1H), 6.89 (s, 1H), 7.32 (m, 10H).

IR (CHCl$_3$); 3600, 3520, 1735, 1600 cm$^{-1}$.

125: NMR (CDCl$_3$); δ0.88 (t, J=7Hz, 3H), 1.15–2.50 (m, 22H), 2.72 (dd, J=17.5, 7.5Hz, 1H), 4.03 (q, J=8Hz, 1H), 5.20–5.47 (m, 3H), 5.61 (dt, J=15, 6Hz, 1H), 6.88 (s, 1H), 7.32 (m, 10H).

IR (CHCl$_3$); 3590, 1735, 1600 cm$^{-1}$.

EXAMPLE 55

Preparation of (5Z,13E,9S)-9-hydroxy-11-oxo-5,13-prostadienoic acid (compound 126)

The compound 124 obtained above (47 mg, 0.094 mmole) and anisole (50 μl, 0.46 mmole) were dissolved in methylene chloride (2.5 ml), and the solution was cooled to −40° C., and a solution of aluminum chloride (32 mg, 0.23 mmole) in nitromethane (1 ml) was added thereto. The mixture was allowed to warm to −10° C. over 30 minutes, and saturated brine was added thereto. To the mixture was added ether to form two separate phases, and the aqueous phase was extracted with ethyl acetate. The extract was combined with the above organic phase, and the combined extract was washed with saturated brine, and dried over anhydrous magnesium sulfate. The dried extract was evaporated to yield an yellow oil (56 mg). The oil was chromatographed over silicic acid (1.1 g), eluting ethyl acetate-n-hexane (1.20–1:1), to yield the title compound 126 (24 mg, 77%) as a colorless oil.

NMR (CDCl$_3$); δ0.89 (t, J=7Hz, 3H), 1.15–2.55 (m, 23H), 2.78 (dd, J=12.5, 7.5Hz, 1H), 4.47 (m, W½=7Hz, 1H), 5.21 (dd, J=15, 7.5Hz, 1H), 5.38–5.70 (m, 3H).

IR (CHCl$_3$); 3500, 3454, 2660 (broad), 1735, 1707 cm$^{-1}$.

EXAMPLE 56

Preparation of (5Z,13E,11R)-9-oxo-11-hydroxy-5,13-prostadienoic acid (compound 127)

The compound 125 obtained above (40 mg, 0.08 mmole) and anisole (43 μl, 0.4 mmole) were dissolved in methylene chloride (2 ml), and the solution was cooled to −40° C., and a solution of aluminum chloride (27 mg, 0.2 mmole) in nitromethane (1 ml) was added thereto. Then, the mixture was treated following the procedure similar to that of Example 55 to yield the title compound 127 (25 mg, 92%) as a colorless oil.

NMR (CDCl$_3$); δ0.89 (t, J=7Hz, 3H), 1.15–2.50 (m, 23H), 2.75 (dd, J=17.5, 7.5Hz, 1H), 4.07 (q, J=8Hz, 1H), 5.25–5.55 (m, 3H), 5.66 (dt, J=15, 6Hz, 1H).

IR (CHCl$_3$); 3586, 3500, 3400, 2660 (broad), 1737, 1707 cm$^{-1}$.

EXAMPLE 57

Preparation of (5Z,13E)-11-oxo-5,9,13-prostatrienoic acid diphenylmethyl ester (compound 128)

The compound 124 obtained above (150 mg, 0.3 mmole) was dissolved in methylene chloride (3 ml), and to the solution, triethylamine (0.125 ml, 0.9 mmole) and methanesulfonyl chloride (35 μl, 0.45 mmole) were added under ice cooling. After the solution was stirred under ice cooling for 30 minutes, the reaction was chromatographed over silica gel (1.5 g), eluting with ethyl acetate-n-hexane (1:4), to yield the title compound 128 (136 mg, 94%) as a pale yellow oil.

NMR (CDCl$_3$); δ0.88 (t, J=7Hz, 3H), 1.15-2.50 (m, 18H), 2.55 (dd, J=7.5, 2Hz, 1H), 2.73 (m, 1H), 5.20-5.70 (m, 4H), 6.12 (dd, J=6, 2Hz, 1H), 6.89 (s, 1H), 7.32 (m, 10H), 7.51 (dd, J=6, 2Hz, 1H).

IR (CHCl$_3$); 1726, 1701, 1586 cm$^{-1}$.

EXAMPLE 58

Preparation of (5Z,13E)-11-oxo-5,9,13-prostatrienoic acid (compound 129)

The compound 128 obtained above (123 mg, 0.25 mmole) and anisole (0.136 ml, 1.25 mmole) were dissolved in methylene chloride (5 ml), and the solution was cooled to −40° C., and a solution of aluminum chloride (84 mg, 0.625 mmole) in nitromethane (2.5 ml) was added thereto. Then, the mixture was treated following the procedure similar to that of Example 55 to yield the title compound 129 (60 mg, 75%) as a colorless oil.

NMR (CDCl$_3$); δ0.88 (t, J=7Hz, 3H), 1.15-2.45 (m, 19H), 2.58 (dd, J=7.5, 2Hz, 1H), 2.78 (m, 1H), 5.25-5.70 (m, 4H), 6.16 (dd, J=6, 2Hz, 1H), 7.57 (dd, J=6, 2Hz, 1H).

IR (CHCl$_3$); 2670 (broad), 1703, 1586 cm$^{-1}$.

EXAMPLE 59

Preparation of (5Z,13E)-9-oxo-5,10,13-prostatrienoic acid diphenylmethyl ester (compound 130)

The compound 125 obtained above (150 mg, 0.3 mmole) was dissolved in methylene chloride (3 ml), and to the solution, triethylamine (0.125 ml, 0.9mmole) and methanesulfonyl chloride (35 μl, 0.45 mmole) were added under ice cooling. Then, the mixture was treated following the procedure similar to that of Example 57 to yield the title compound 130 (135 mg, 93%) as a colorless oil.

NMR (CDCl$_3$); δ0.88 (t, J=7Hz, 3H), 1.15-2.55 (m, 19H), 3.13 (m, 1H), 5.20-5.60 (m, 4H), 6.13 (dd, J=6, 2Hz, 1H), 6.88 (s, 1H), 7.32 (m, 10H), 7.45 (dd, J=6, 2Hz, 1H).

IR (CHCl$_3$); 1725, 1698, 1584 cm$^{-1}$.

EXAMPLE 60

Preparation of (5Z,13E)-9-oxo-5,10,13-prostatrienoic acid (compound 131)

The compound 130 obtained above (123 mg, 0.25 mmole) and anisole (0.136 ml, 1.25 mmole) were dissolved in methylene chloride (5 ml), and the solution was cooled to −40° C., and a solution of aluminum chloride (84 mg, 0.625 mmole) in nitromethane (2.5 ml) was added thereto. Then, the mixture was treated following the procedure similar to that of Example 55 to yield the title compound 131 (66 mg, 83%) as a colorless oil.

NMR (CDCl$_3$); δ0.88 (t, J=7Hz, 3H), 1.15-2.60 (m, 20H), 3.17 (m, 1H), 5.25-5.60 (m, 4H), 6.14 (dd, J=6, 2Hz, 1H), 7.49 (dd, J=6, 2Hz, 1H).

IR (CHCl$_3$); 2670 (broad), 1701, 1583 cm$^{-1}$.

The comprehensive scheme illustrating the reactions described in Examples 53-63 is shown below.

Reaction scheme for preparation of 15-deoxy PGD$_2$, 15-deoxy PGE$_2$, 15-deoxy PGJ$_2$, 15-deoxy PGA$_2$, (Example 53-60)

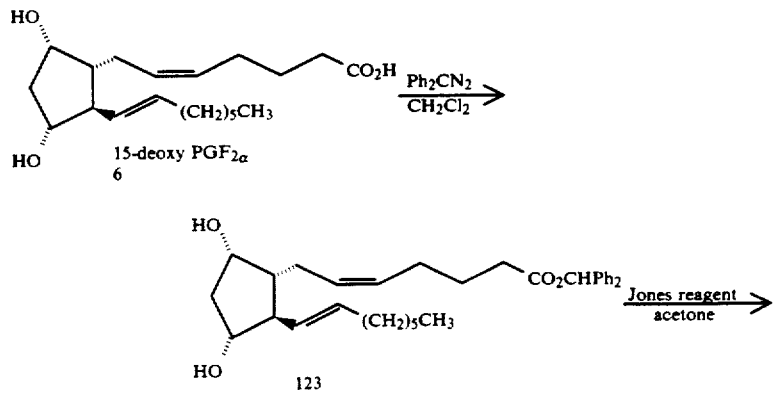

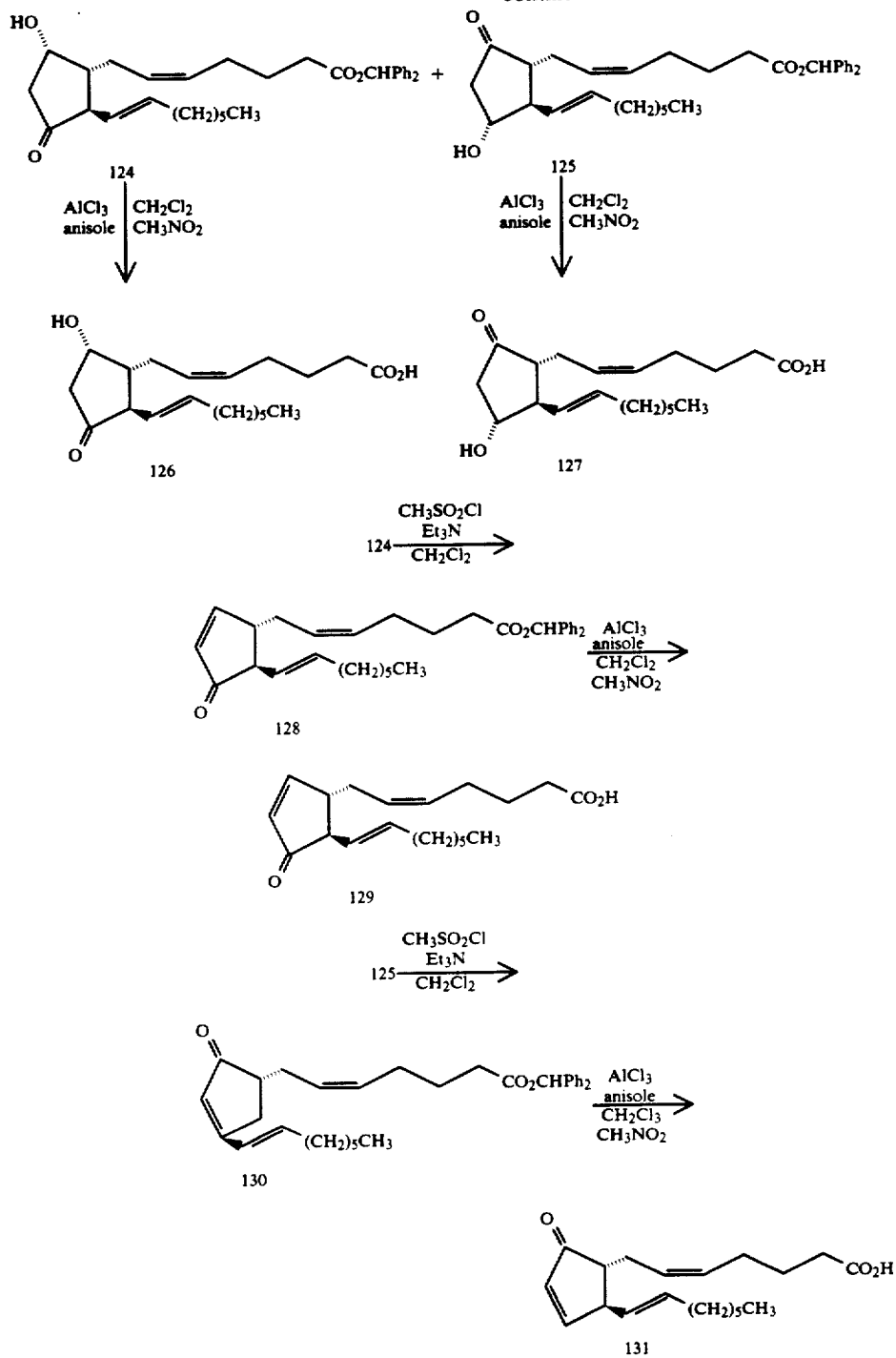

-continued

PHARMACOLOGICAL TEST

The compounds of the invention were tested for their pharmacological activities. The results of the tests are provided below.

TEST 1

Cats (3.0–6.5 kg) were anesthetized with ketamine (10 mg/kg, i.m), and 0.4% oxybuprocaine was applied to the animals' eyes in the form of an eye drop. The intraocular pressure was measured using applanation pneumatonometer (Japan Alcan Inc.).

The test compounds were suspended in physiological saline. Each 25 μl portion of the suspensions was applied to either one of eyes of the animals, and the contralateral eye received 25 μl of physiological saline. The intraocular pressure was measured at 0.5, 1, 2, 3 hours after administration. One group comprised 3–6 animals.

The results are shown in Table 1. The numerical values in the table are the mean of the differences between intraocular pressure values for the treated eye and control eye.

TABLE 1

| Compound No. | dose (μg) | difference (mmHg) |
|---|---|---|
| 6 | 50 | 4.4 |
| 6 | 10 | 2.0 |
| 6' | 50 | 1.1 |
| 7 | 50 | 6.2 |
| 7 | 10 | 1.3 |
| 8 | 50 | 3.7 |
| 8 | 10 | 2.1 |
| 8' | 50 | 3.4 |
| 12 | 50 | 1.1 |
| 13 | 50 | 0.7 |
| 21 | 50 | 5.1 |
| 28 | 50 | 3.0 |
| 28' | 50 | 2.0 |
| 29 | 50 | 3.8 |
| 29' | 50 | 1.3 |
| 110 | 100 | 1.2 |
| 119 | 100 | 2.2 |
| 122 | 100 | 2.4 |
| 126 | 100 | 0.3 |
| 127 | 100 | 2.2 |
| 129 | 100 | 0.2 |
| 131 | 100 | 1.0 |
| A | 50 | 5.0 |
| B | 50 | 2.8 |
| C | 50 | 5.8 |
| D | 50 | 4.5 |
| E | 50 | 2.4 |

A: PGE$_2$
B: PGF$_{2\alpha}$
C: PGF$_{2\alpha}$ isopropyl ester
D: 13,14-dihydro-15-keto PGF$_{2\alpha}$
E: 20-ethyl-13,14-dihydro-15-keto PGF$_{2\alpha}$ isopropylester The above results apparently demonstrate that 15-deoxy PG derivatives have significant intraocular pressure-reducing activity.

TEST 2

Test compounds was administered topically to eye of Rhesus monkey (female, 4.2-6.1 kg), and the intraocular pressure was measured over four hours. The intraoccular pressure was measured using applanation pneumatonometer (Japan Alcan Inc.) after surface anesthesia treatment with 0.4% oxybuprocaine. The test compounds were suspended in physiological saline. Each 25 μl portion of the suspension was applied to either one of the eyes of the animals, and the contralateral eye received 25 μl of only physiological saline as a control. One group comprised 3-7 animals. The results are shown in Table 2. The numerical values in the table are the mean of the differences between intraocular pressure values of the treated eye and control eye.

As shown in Table 2, each of 15-deoxy PG derivatives is an effective intraocular pressure-reducing agent in monky. Additionaly, Table 2 also demonstrates that the 15-deoxy PG derivatives are equivalent to or more than timolol maleate in their activities, which is currently used most frequently in clinial field.

TABLE 2

| Compound No. | dose (μg) | difference (mmHg) |
|---|---|---|
| 6 | 20 | 3.0 |
| 6 | 50 | 3.4 |
| 7 | 50 | 2.8 |
| 8 | 10 | 1.0 |
| 8 | 50 | 2.7 |
| timolol maleate | 100 | 3.2 |

TEST 3

Possible side effects which may be produced by the test compounds of the invention were examined using rabbits (male, 2.2-2.5 kg) fixed to a rabbit retainer. The test compounds were suspended in physiological saline. Each 25 μl portion of the suspension was administered to either one of the eyes of the animals, and the contralateral eye received 25 μl of physiological saline as a control. According to the criteria described in Y. Goh, M. Nakajima, I. Azuma and O. Hayaishi, *Jpn. J. Ophthalmol.*, 32, 4-71(1988), the side effects such as conjunctival hyperemia, iris hyperemia, and irritation (which was judged from lid closing response) were observed over four hours after ophthalmic administration. One group comprised 3-5 animals. The results are shown in Table 3. The data in Table 3 illustrate typical values.

The evaluations were carried out using following symbols; —: non-reaction, ±: weak reaction, +: apparent reaction, and ++: strong reaction The results in Table 3 apparently demonstrate that all of the 15-deoxy PG derivatives are much lower in their side effects. Particularly, the 15-deoxy PG derivatives are siginificatly lower in side effect than PGF$_{2\alpha}$ and PGF$_{2\alpha}$ isopropyl ester which are recommended in Japanese Patent Publication No. 1418/1984, and the known 13,14-dihydro-15-keto PG derivatives.

TABLE 3

| Compound No. | Dose (μg) | Side effect C.H.[1] | I.H.[2] | IR[3] |
|---|---|---|---|---|
| 6 | 100 | — | — | — |
| 6 | 50 | — | — | — |
| 6' | 100 | ± | — | — |
| 6' | 50 | — | — | — |
| 7 | 50 | — | — | — |
| 7 | 10 | — | — | — |
| 8 | 50 | — | — | — |
| 8 | 10 | — | — | — |
| 8' | 50 | ± | — | — |
| 12 | 50 | — | — | — |
| 13 | 50 | — | — | — |
| 21 | 50 | ± | — | — |
| 28 | 50 | — | — | — |
| 28' | 50 | ± | — | — |
| 29 | 50 | ± | — | — |
| 29' | 50 | — | — | — |
| 110 | 100 | + | ± | — |
| 119 | 100 | — | — | — |
| 122 | 100 | — | — | — |
| 126 | 100 | ± | ± | — |
| 127 | 100 | ∓ | + | + |
| 129 | 100 | + | ± | ± |
| 131 | 100 | ± | ± | ± |
| A | 50 | ++ | ++ | ++ |
| B | 50 | ++ | ++ | ++ |
| C | 50 | ++ | ++ | ++ |
| D | 50 | ± | ++ | — |
| E | 50 | ++ | ++ | ++ |
| F | 50 | ++ | + | — |
| G | 50 | + | ++ | — |
| H | 50 | ++ | ++ | — |

A: PGE$_2$
B: PGF$_{2\alpha}$
C: PGF$_{2\alpha}$ isopropyl ester
D: 13,14-dihydro-15-keto PGF$_{2\alpha}$
E: 20-ethyl-13,14-dihydro-15-keto PGF$_{2\alpha}$ isopropylester
F: 15-keto PGF$_{2\alpha}$
G: 9β-PGF$_{2\alpha}$
H: 15-(R) PGF$_{2\alpha}$
[1] conjunctival hyperemia
[2] iris hyperemia
[3] irritation

TEST 4

The test compounds were applied to the eyes of rabbits (male, 2.2–2.5 kg) fixed to rabbit retainer, and the intraocular pressure was measured at 0, 0.5, 1, 2, 3 hours after administration. After conducting surface anesthesia treatment with 0.4% oxybuprocaine, the intraocular pressure was measured using applanation pneumatonometer (Japan Alcan Inc.). The test compounds were suspended in physiological saline, and each 25 μl portion of the suspension was administered to either one of the eyes of the animals and the contralateral eye received 25 μl of physiological saline as a control. One group comprised 3–4 animals. The results are shown in Table 4. The numerical values in the table are the mean (±SEM) of the results of each of the animals.

As shown in Table 4, 15-deoxy PG derivatives exhibit no initial increase in intraocular pressure, which would be produced by $PGF_{2\alpha}$ or $PGF_{2\alpha}$ isopropyl ester.

TABLE 4

| Compound | Dose (μg) | | Time (hr) | | | | |
|---|---|---|---|---|---|---|---|
| | | | 0 | 0.5 | 1.0 | 2.0 | 3.0 |
| 6 | 200 | TE | 17.4 ± 0.3 | 18.6 ± 0.5 | 17.5 ± 0.5 | 16.5 ± 0.8 | 15.10.8 |
| | | CE | 17.4 ± 0.5 | 18.5 ± 1.4 | 18.8 ± 0.5 | 18.1 ± 1.4 | 19.1 ± 1.2 |
| 8 | 200 | TE | 16.8 ± 0.3 | 14.2 ± 0.9 | 13.5 ± 0.8 | 15.0 ± 1.2 | 15.3 ± 1.1 |
| | | CE | 16.8 ± 0.8 | 16.5 ± 0.5 | 16.3 ± 1.2 | 17.7 ± 1.4 | 18.0 ± 0.9 |
| B | 50 | TE | 17.1 ± 0.6 | 22.3 ± 0.3 | 19.0 ± 1.2 | 16.5 ± 1.3 | 12.3 ± 1.1 |
| | | CE | 17.5 ± 0.9 | 17.8 ± 0.9 | 17.6 ± 0.5 | 18.1 ± 1.2 | 18.4 ± 0.8 |
| C | 50 | TE | 21.0 ± 2.1 | 23.2 ± 0.9 | 20.8 ± 0.3 | 13.0 ± 0.5 | 12.5 ± 0.3 |
| | | CE | 20.8 ± 1.4 | 18.8 ± 0.9 | 19.0 ± 1.2 | 17.5 ± 0.3 | 21.0 ± 1.3 |

TE: treated eye, CE: control eye
B: $PGF_{2\alpha}$
C: $PGF_{2\alpha}$ isopropyl ester

STABILITY TEST

The following description shows procedures and results of stability test of the compounds of the invention.

TEST 5

The crystal (10.65 mg) of 15-deoxyprostaglandin $F_{2\alpha}\cdot Na$ (Example 36) was dissolved in 10 ml of 0.05M phophate buffer (pH 6.5). The solution was filtered through the membrane (Millipore, MILLEX-HV) to yield 0.1% solution (pH 6.5). The stability test was carried out on the resultant solution to give the data as shown in Tables 5 and which are described hereinafter.

TEST 6

The crystal (10.84 mg) of 15-deoxyprostaglandin $F_{2\alpha}\cdot Na$ was dissolved in 10 ml of 0.05M phophate buffer (pH 7.0). The solution was filtered through the membrane (Millipore, MILLEX-HV) to yield 0.1% solution (pH 7.0). The stability test was carried out on the resultant solution to give the data as shown in Tables 5 and 6 which are described hereinafter.

TEST 7

The crystal (10.35 mg) of 15-deoxyprostaglandin $F_{2\alpha}\cdot Na$ was dissolved in 10 ml of 0.05M phophate buffer (pH 7.5). The solution was filtered through the membrane (Millipore, MILLEX-HV) to yield 0.1% solution (pH 7.4). The stability test was carried out on the resultant solution to give the data as shown in Tables 5 and 6 which are described hereinafter.

TEST 8

The crystal (1.10 mg) of 15-deoxyprostaglandin $F_{2\alpha}\cdot Na$ was dissolved in 10 ml of 0.05M phophate buffer (pH 7.5). The solution was filtered through the membrane (Millipore, MILLEX-HV) to yield 0.01% solution (pH 7.4). The stability test was carried out on the resultant solution to give the data as shown in Table 5 which is described hereinafter.

TABLE 5

Results of stability test of 15-deoxy $PGF_{2\alpha}\cdot Na$ solutions in boiling water bath (remaining %)

| Time (hours) | 2 | 4 | 6 | 8 |
|---|---|---|---|---|
| Test 5 (0.1%, pH 6.5) | 102.9% | 101.9% | 101.9% | 101.7% |
| Test 6 (0.1%, pH 7.0) | 100.9% | 100.0% | 101.1% | 99.8% |
| Test 7 (0.1%, pH 7.4) | 101.2% | 98.9% | 99.6% | 102.9% |
| Test 8 (0.01%, pH 7.4) | 100.9% | 101.4% | 103.5% | 102.4% |

TABLE 6

Results of accelerated stability test of 15-deoxy $PGF_{2\alpha}\cdot Na$ solutions (remaining %)

| | 60° C. | | 50° C. | | 40° C. |
|---|---|---|---|---|---|
| Time (months) | 0.5 | 1 | 0.5 | 1 | 1 |
| Test 5 | 101.1% | 98.4% | 98.6% | 98.4% | 102.8% |
| Test 6 | 101.6% | 101.2% | 101.8% | 100.4% | 100.3% |
| Test 7 | 97.3% | 98.1% | 99.8% | 99.1% | 97.6% |

TEST 9

The crystal (10.29 mg) of 15-deoxyprostaglandin $F_{2\alpha}\cdot Na$ was dissolved in 10 ml of 0.05M phosphate buffer (pH 7.5) to which 0.05% methylparaben, 0.02% propylparaben, and 0.6% sodium chloride had been added. The solution was filtered through the membrane (Millipore, MILLEX-GV) to yield 0.1% solution (pH 7.2) which is useful as an eye drop. The stability test was carried out on the resultant solution to give the data as shown in Tables 7 and 8 which are described hereinafter.

TEST 10

The crystal (1.06 mg) of 15-deoxyprostaglandin $F_{2\alpha}\cdot Na$ (Example 36) was dissolved in 10 ml of 0.05M phophate buffer (pH 7.5) to which 0.05% methylparaben, 0.02% propylparaben, and 0.6% sodium chloride had been added. The solution was filtered through the membrane (Millipore, MILLEX-GV) to yield 0.01% solution (pH 7.2) which is useful as an eye drop. The stability test was carried out on the resultant solution to give the data as shown in Tables 7 and 8 which are described hereinafter.

TABLE 7

Results of stability test of 15-deoxy PGF$_{2\alpha}$.Na solutions in boiling water bath (remaining %)

| Time (hours) | 2 | 4 | 6 | 9 |
|---|---|---|---|---|
| Test 9 (0.1%) | 100.6% | 99.6% | 99.4% | 100.4% |
| Test 10 (0.01%) | 99.2% | 99.7% | 98.9% | 99.6% |

TABLE 8

Results of accelerated stability test of 15-deoxy PGF$_{2\alpha}$.Na solutions (remaining %)

| | 60° C. | | 50° C. | | 40° C. |
|---|---|---|---|---|---|
| Time (months) | 0.5 | 1 | 0.5 | 1 | 1 |
| Test 9 | 100.5% | 101.3% | 98.8% | 98.6% | 98.4% |
| Test 10 | 98.4% | 97.4% | 98.0% | 98.7% | 99.2% |

The above data demonstrates that the formulations of the invention are really stable. This results show that the formulations are useful for pharmaceutical use.

FORMULATION 1

1. Preparation

The components described in the following table were weighed as indicated. To the weighed components, 250 ml of injectable distilled water was added. If necessary, the mixture was heated to 40°±5° C. to dissolve the components completely. After dissolving the components (and after cooling the solution if necessary), additional injectable distilled water was added thereto to adjust the volume to exactly 300 ml, which gave a bulk solution for eye drops.

The solution was filtered through a disposable filter unit (0.22 μm, Nalgene Disposable Filterware) in a clean bench, and the filtrate was stored until the next step for portioning.

2. Portioning

The solution prepared above was placed into a disposable filter unit (0.22 μm, Millipore Mylecks GS) was attached to the tip of the syringe. Then, while the solution was filtered through the filter unit under sterile conditions, the filtered solution was directly portioned into a sterilized container for eye drops (Taisei Kako, BP-5C) at a ratio of 5 ml solution per container. The containers containing the sterilized solution were capped with inner plugs (Taisei Kako, CN-5D) and then with outer caps (Taisei Kako, CAB-10) to form products The above procedures were conducted under sterile conditions.

TEST 11

Rhesus monkeys (female, 4–6 kg) were slightly anesthetized with ketamine (5 mg/kg, i.m.), and then 0.4% oxybuprocaine was applied to the animals, eyes in the form of an eye drop. Then, the intraocular pressure was measured using an applanation pneumatonometer (Japan Alcon Inc.).

The test compound was dissolved in a vehicle for eye drop (0.05M phosphate buffer containing 0.1% methyl paraben, 0.02% propyl paraben, and 0.6% sodium chloride). Twenty five μl portion of the solution was applied to either one of the eyes of the animals. The contralateral eye received 25 μl of the vehicle which was free of the test compound. The intraoccular pressure was measured at 2, 4, and 6 hours after application.

One group comprised 6 animals. The results are shown in Table 10. The numerical values in the table are the mean of the differences in the intraocular pressure (IP) (i.e., IP values of the control eye-IP values of the treated eye) of 3 points at 2, 4 and 6 hours after application.

TABLE 10

| Test Compound | dose (μg) | difference (mmHg) |
|---|---|---|
| Sodium salt of 6 | 25 | 0.75 |
| | 50 | 1.50 |
| | 100 | 2.15 |
| | 250 | 2.45 |

The results in Table 10 show that the intraocular pressure-reducing effect of the compound 6 is dependent on dose.

TEST 12

Rhesus monkeys (female, 4–6 kg) were slightly anesthetized with ketamine {5 mg/kg, i.m.), and then 0.4% oxybuprocaine was applied to the animals, eyes in the form of an eye drop. Then, the intraocular pressure was measured using an applanation pneumatonometer (Japan Alcan Inc.).

The test compound was applied to either one of the eyes of the animals as one drop of the 0.33% preparation for eye drop (the test compound is about 100 μg). The contralateral eye received the same volume of the vehicle which was free of the test compound. The application to the eye was conducted twice a day (at AM 9:00 and PM 4:30), and continued three months. Measurement of the intraoccular pressure was conducted with two weeks intervals, and the pressure was measured at 2, 4, and 6 hours after application on the day when the measurement was conducted.

One group comprised 7 animals. The results are shown in Table 11. The numerical values in the table are the mean of the differences in the intraocular pressure (IP) (i.e., IP values of the control eye—IP values of the

| | Amounts of Components | | | | |
|---|---|---|---|---|---|
| | Amounts of Components for Preparations of: | | | | |
| Components | 0.1% | 0.2% | 0.3% | 0.4% | 0.33% |
| Sodium salt of compound 6 | 300 mg | 600 mg | 900 mg | 1200 mg | 1000 mg |
| methyl p-hydroxybenzoate | 300 mg | 300 mg | 300 mg | 300 mg | 300 mg |
| propyl p-hydroxybenzoate | 60 mg | 60 mg | 60 mg | 60 mg | 60 mg |
| 1 sodium phosphate 2 hydrate | 330 mg | 330 mg | 330 mg | 330 mg | 330 mg |
| 2 sodium phosphate 12 hydrate | 4.62 g | 4.62 g | 4.62 g | 4.62 g | 4.62 g |
| sodium chloride | 1.80 g | 1.80 g | 1.80 g | 1.80 g | 1.80 g |

The amounts of the compound 6 in one drop of the 0.1%, 0.2%, 0.3%, 0.4%, and 0.33% preparations are about 30 μg, 60 μg, 90 μg, 120 μg, and 100 μg, respectively.

treated eye) of 3 points at 2, 4 and 6 hours after application.

TABLE 11

| days | difference (mmHg) | | | | | | |
|---|---|---|---|---|---|---|---|
| | 0 | 14 | 28 | 42 | 56 | 70 | 84 |
| Sodium salt of 6 | 2.20 | 2.02 | 2.24 | 2.03 | 2.01 | 2.09 | 2.14 |
| timolol maleate | 2.73 | 2.54 | 1.10 | 1.26 | 1.20 | 1.26 | 1.22 |

It is known that the intraocular pressure-reducing effect of timolol maleate, which is most broadly used in clinical field, is lowered in association with the lapse of the application term. The results in Table 11 shows that the intraocular pressure-reducing effect of the sodium salt of the compound 6 is not lowered even if it is used in a long duration, which is an advantage of the compound of the present invention over timolol maleate.

What is claimed is:

1. A method for treating hypertension or glaucoma in the eye comprising contacting the surface of the eye with a therapeutic amount of a 15-deoxyprostaglandin derivative of the formula (I):

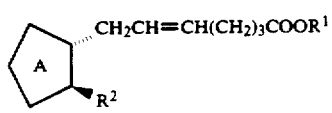

in which

is a 5 membered ring which is selected from a group consisting of

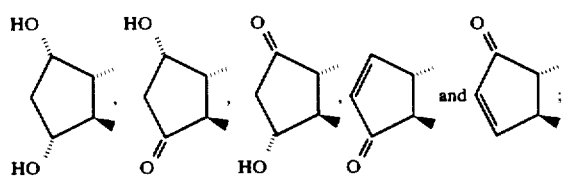

$R^1$ is hydrogen or lower alkyl;

$R^2$ is $C_6-C_{12}$ alkyl, $C_6-C_{12}$ alkenyl or $C_6-C_{12}$ alkadienyl or a pharmaceutically acceptable salt thereof.

2. The method as claimed in claim 1, wherein the compound as indicated in claim 1 is periodically contacted with the surface of the eye.

3. The method as claimed in claim 1, wherein (5Z,13E,9S,11R)-9,11-dihydroxy-5,13-prostadiehoic acid of the formula (I):

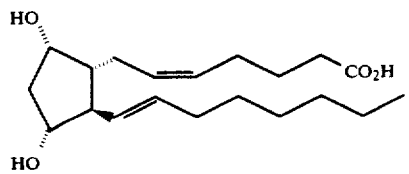

or a pharmaceutically acceptable salt or a lower salt alkyl ester is periodically contacted with the surface of the eye at a dose of 1 μg/eye/day to 1000 μg/eye/day.

4. A kit for delivery of a topical solution for treatment of hypertension or glaucoma in the eye which comprises:

(a) container having a solution including a compound of the formula (I), and (b) means for topical delivery of said solution to the eye in a controlled dosage.

5. The kit as claimed in claim 4, wherein the compound is (5Z,13E,9S,11R)-9,11-dihydroxy-5,13-prostadienoic acid of the formula (I):

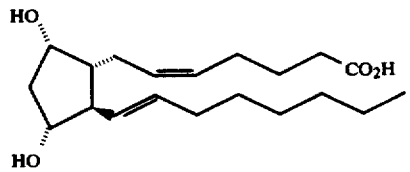

or a pharmaceutically acceptable salt or a lower alkyl ester.

6. The method as claimed in claim 1, wherein

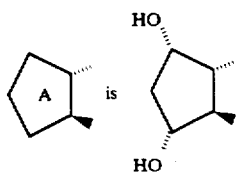

7. The method as claimed in claim 1, wherein $R^2$ is $C_6-C_{12}$ alkenyl.

8. The method as claimed in claim 7, wherein $R^2$ is $C_8-C_{10}$ alkenyl.

9. The method as claimed in claim 8, wherein $R^2$ is a straight-chain $C_8-C_{10}$ alkenyl.

10. The method as claimed in claim 6, wherein $R^2$ is $C_6-C_{12}$ alkenyl.

11. The method as claimed in claim 10, wherein $R^2$ is $C_8-C_{10}$ alkenyl.

12. The method as claimed in claim 11, wherein $R^2$ is a straight-chain $C_8-C_{10}$ alkenyl.

13. The kit as claimed in claim 4, wherein

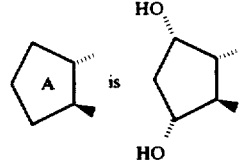

14. The kit as claimed in claim 4, wherein $R^2$ is $C_6-C_{12}$ alkenyl.

15. The kit as claimed in claim 14, wherein $R^2$ is $C_8-C_{10}$ alkenyl.

16. The kit as claimed in claim 15, wherein $R^2$ is a straight-chain $C_8-C_{10}$ alkenyl.

17. The kit as claimed in claim 13, wherein $R^2$ is a $C_6-C_{12}$ alkenyl.

18. The kit as claimed in claim 17, wherein $R^2$ is $C_8-C_{10}$ alkenyl.

19. The kit as claimed in claim 18, wherein $R^2$ is a straight-chain $C_8-C_{10}$ alkenyl.

* * * * *

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

On the title page, under item [56],
In the heading OTHER PUBLICATIONS, Column 2, line 17, "Trhomboxane" should read -- Thromboxane--.

Column 1, line 34, "oxgen" should read --oxygen--.
line 48, "PGF2α" should read --$PGF_{2\alpha}$--.

Column 2, line 15, "intaocular" should read --intraocular--.
line 16, "embodimet" should read --embodiment--.
line 53, "haydrocarbon" should read --hydrocarbon--.

Column 3, line 38, please insert --.-- after "vol".
line 39, please delete the first occuring ",".
line 53, please delete the fourth occuring "," following the second occurring "N".

Column 4, line 1, "preferablly" should read --preferably--.
line 7, "compoumd" should read --compound--.
line 21, please insert --about-- following "is".

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

line 28, please delete "," following "periodically".

Column 5, line 22, delete "HO" and insert --RO--.

line 34, "2-methoxyethoxyethyl" should read --2-methoxyethoxymethyl--.

Column 6, line 23, please insert --.-- following "reaction".

Column 7, line 56, "preferablly" should read --preferably--.

Column 8, line 50, "temparature" should read --temperature--.

Column 9, line 4, "ocetnyl" should read --octenyl--.

line 67, "gas" should read --was--.

Column 10, line 25, "1.0" should read --4.0--.

line 46, "colum" should read --column--.

line 67, "3 92" should read --3.92--.

Column 11, line 9, "pottasium" should read --potassium--.

line 54, "discolsed" should read --disclosed--.

UNITED STATES PATENT AND TRADEMARK OFFICE
CERTIFICATE OF CORRECTION

PATENT NO. : 5,292,754  Page 3 of 9
DATED : March 8, 1994
INVENTOR(S) : KISHI et al.

It is certified that error appears in the above-indentified patent and that said Letters Patent is hereby corrected as shown below:

line 66, "compounds" should read --compound--.

Column 12, line 37, "CDC$_{13}$" should read --CDCL$_3$--.

line 64, "6" should read --6'--.

Column 13, line 6, "[m,4H)" should read --(m,4H)--.

Column 15, line 6, "CHC$_3$" should read --CHCL$_3$--.

line 40, "CDC$_{13}$" should read --CDCL$_3$--.

Column 16, line 48, please insert --)-- after "mmole".

line 59, "(2H)" should read --2H)--.

Column 17, line 2, "under one hydrogen at atmospheric" should read --under hydrogen at one atmospheric--.

line 15, "obtainer" should read --obtained--.

line 27, please insert --3.75-4.15 (m,2H),-- before "4.65".

line 33, "dropyranylo>.y" should read --dropyranyloxy--.

line 61, "c-s" should read --cis--.

Column 18, line 61, please delete "." after "1.0-2.5" and insert --(--.

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

Column 21, line 51, "prosedure" should read --procedure--.
        Column 22, line 23, "obove" should read --above--.
            line 47, "stirrd" should read --stirred--.
        Column 23, line 11, "25" should read --25'--.
            line 24, "-30" should read ---30°C--.
            line 55, "obove" should read --above--.
    Column 24, lines 8-9, complete the right alpha bond as labeled.
        lines 18-19, complete the right alpha bond as labeled.
        lines 28-29, complete the right alpha bond as labeled.
        line 42, connect the beta bond to the carbon molecule as labeled.
        lines 60-61, complete the right alpha bond as labeled.
    Column 26, line 37, "stirrd" should read --stirred--.
        line 42, "temparature" should read --temperature--.

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

Column 27, line 28, "stirrd" should read --stirred--.
Column 29, line 9, "colum" should read --column--.
    line 23, "obove" should read --above--.
    lines 51-52, insert an alpha bond between the oxygen and carbon molecules as labeled.
    lines 61-62, insert an alpha bond between the oxygen and carbon molecules as labeled.
Column 30, lines 7-8, insert an alpha bond between the oxygen and carbon molecules as labeled.
    lines 18-19, insert an alpha bond between the oxygen and carbon molecules as labeled.
    lines 28-29, insert an alpha bond between the oxygen and carbon molecules as labeled.
    lines 38-39, insert an alpha bond between the oxygen and carbon molecules as labeled.
Column 31, line 35, "exess" should read --excess--.
Column 32, line 53, "13prostadienoic" should read --13-prostadienoic--.
    line 66, please insert --δ-- before "0.89".

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

Column 33-34, reaction # 2, replace the beta bond with an alpha bond between the oxygen and carbon molecules as labeled.

reaction # 115, replace the alpha bond with a beta bond as labeled.

Column 36, line 63, please delete ")" following "=7Hz".

Column 38, line 42, "1.20" should read --1:20--.

Column 40, line 37, "63" should read --60--.

Column 41-42, reaction # 130, move the beta bond from carbon position 4 to carbon position 3 as labeled.

Column 41-42, reaction # 130, "$CH_2Cl_3$" should read --$CH_2Cl_2$--.

Column 43, Table 1, line 29, "PGE2" should read --$PGE_2$--.

line 43, "Alcan" should read --Alcon--.

line 55, "monky" should read --monkey--.

line 55, "Additionaly" should read --Additionally--.

line 58, "clinial" should read --clinical--.

Column 44, Table 3, line 50, "=" should read --+--.

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

Column 45, line 9, "Alcan" should read --Alcon--.

line 19, "produed" should read --produced--.

line 41, "$F_{2\alpha} \cdot N_a$" should read --$F_{2\alpha} \cdot Na$--.

line 42, "phophate" should read --phosphate--.

line 46, please insert --6-- before "which".

line 50, "phophate" should read --phosphate--.

line 59, "phophate" should read --phosphate--.

line 68, "phophate" should read --phosphate--.

Column 45-46, Table 4, line 23, "15.10.8" should read --15.1 ± 0.8--.

Table 4, line 29, "21.0 ± 2.1" should read --21.0 ± 1.2--.

Column 46, line 19, please delete "    TABLE 6    ".

line 36, please insert --    TABLE 6    --.

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

line 48, "phophate" should read --phosphate--.

line 61, "phophate" should read --phosphate--.

Column 47, line 39, please insert --a sterilized disposable syringe (30 ml, Termo), and-- before "a dis-".

line 49, please insert --.-- before "The above".

Column 48, line 5, "animals, eyes" should read --animals' eyes--.

line 37, "{5mg/kg, i.m.)" should read --(5mg/kg, i.m.)--.

line 38, "animals, eyes" should read --animals' eyes--.

UNITED STATES PATENT AND TRADEMARK OFFICE
CERTIFICATE OF CORRECTION

PATENT NO. : 5,292,754
DATED : March 8, 1994
INVENTOR(S) : KISHI et al.

It is certified that error appears in the above-indentified patent and that said Letters Patent is hereby corrected as shown below:

line 41, "Alcan" should read --Alcon--.
  Column 49, Claim 3, line 58, "prostadiehoic" should read --prostadienoic--.

Signed and Sealed this

Sixteenth Day of May, 1995

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,292,754
DATED : March 8, 1994
INVENTOR(S) : Morio Kishi, et al

It is certified that error appears in the above-indentified patent and that said Letters Patent is hereby corrected as shown below:

Column 24, lines 39-40, complete the right alpha bond to read as shown below:

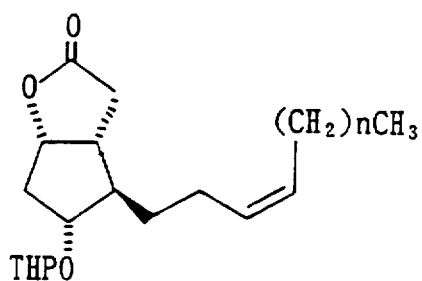

UNITED STATES PATENT AND TRADEMARK OFFICE
CERTIFICATE OF CORRECTION

PATENT NO. : 5,292,754
DATED : March 8, 1994
INVENTOR(S) : Morio KISHI et al.

It is certified that error appears in the above-indentified patent and that said Letters Patent is hereby corrected as shown below:

Column 24, lines 50-51, complete the right alpha bond as shown below labeled;

Signed and Sealed this

Thirtieth Day of January, 1996

Attest:

BRUCE LEHMAN

Attesting Officer

Commissioner of Patents and Trademarks